(12) United States Patent
Rezai et al.

(10) Patent No.: US 7,454,251 B2
(45) Date of Patent: Nov. 18, 2008

(54) EXCESS LEAD RETAINING AND MANAGEMENT DEVICES AND METHODS OF USING SAME

(75) Inventors: Ali R. Rezai, Bratenahl, OH (US); Kenneth B. Baker, Chesterland, OH (US); John D. Hall, Mayfield Heights, OH (US); Frank G. Shellock, Los Angeles, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 689 days.

(21) Appl. No.: 10/749,621

(22) Filed: Dec. 30, 2003

(65) Prior Publication Data

US 2005/0015128 A1    Jan. 20, 2005

Related U.S. Application Data

(60) Provisional application No. 60/474,179, filed on May 29, 2003.

(51) Int. Cl.
*A61N 1/04*    (2006.01)

(52) U.S. Cl. ...................... 607/115; 607/139

(58) Field of Classification Search ............. 607/115, 607/116, 45, 46, 139; 600/372, 373, 383, 600/585, 378; 606/129, 130, 108; 604/174, 604/175

See application file for complete search history.

(56) References Cited

U.S. PATENT DOCUMENTS

| 4,328,813 | A | * | 5/1982 | Ray .......................... 607/139 |
| 5,464,446 | A | | 11/1995 | Dreessen et al. |
| 5,843,150 | A | | 12/1998 | Dreessen et al. |
| 6,044,304 | A | | 3/2000 | Baudino |
| 6,210,417 | B1 | | 4/2001 | Baudino et al. |
| 7,004,948 | B1 | * | 2/2006 | Pianca et al. ................ 606/129 |
| 2002/0052610 | A1 | | 5/2002 | Skakoon et al. |
| 2002/0091419 | A1 | | 7/2002 | Firlik et al. |
| 2005/0004637 | A1 | * | 1/2005 | Singhal et al. .............. 607/116 |

FOREIGN PATENT DOCUMENTS

WO    WO 03/068304 A1 *    8/2003

* cited by examiner

*Primary Examiner*—Angela D. Sykes
*Assistant Examiner*—Alyssa M Alter
(74) *Attorney, Agent, or Firm*—Tarolli, Sundheim Covell & Tummino LLP

(57) ABSTRACT

A device and method for retaining an excess portion of a lead implanted within or on a surface of a brain of a patient is disclosed. The device comprises a burr hole ring configured to be secured to a skull of the patient and a lead retainer extending from the burr hole ring. The lead retainer is configured to store at least a section of the excess portion of the lead.

3 Claims, 21 Drawing Sheets

EXCESS LEAD RETAINING AND MANAGEMENT DEVICES AND METHODS OF USING SAME

CROSS-REFERENCE WITH RELATED APPLICATION

This application claims priority to U.S. Provisional Patent Application No. 60/474,179 filed on May 29, 2003, which is hereby incorporated by reference in its entirety.

BACKGROUND

Deep brain stimulation (DBS) is a surgical option for patients with Parkinson's disease, essential tremor, dystonia, and tremor due to multiple sclerosis. In a typical DBS procedure, a neurostimulation system is implanted into a brain of a patient to electrically stimulate a target site in the patient's brain. One example of a neurostimulation system is an Activa® system manufactured by Medtronic, Inc. of Minneapolis, Minn. The Activa® system includes a stimulation lead, a Soletra® implantable pulse generator, and an extension lead. One type of stimulation lead includes four thin, insulated, coiled wires terminating into four 1.5 mm electrodes at its distal end and terminating into a connector at its proximal end. The stimulation lead is housed within a polyurethane jacket such that the diameter of the stimulation lead is 1.27 mm. The stimulation lead typically comes in two lengths, 40 cm and 28 cm. The implantable pulse generator (IPG) provides electronic pulses to the electrodes at the distal end of the stimulation lead. The extension lead includes a mating connector at one end to connect to the connector at the distal end of the stimulation lead. The extension lead also includes a male plug connector that connects to a female connection port provided on the IPG. Typically, the extension lead has a length of about 51 cm.

In a typical surgical procedure to implant the neurostimulation system for DBS, the surgical procedure begins with placing a stereotactic headframe around a patient's head to keep the patient's head stationary. The stereotactic headframe also helps guide a surgeon in the placement of a lead used for neurostimulation. Next, the surgeon takes an image of the patient's brain using sophisticated imaging equipment, such as a computed tomography (CT) or magnetic resonance imaging (MRI), to map the brain and localize a target site within the brain. Once the surgeon maps the brain, a local anesthetic is given to the patient. The surgeon then makes a small incision approximately 4 cm long that provides an approximately 3 cm×3 cm opening in the patient's scalp. Next, the surgeon drills a 14 mm diameter burr hole into the patient's skull to provide access to the patient's brain in preparation for the implantation of the lead.

The surgeon then inserts a temporary recording stimulation lead into the target site of the brain to test the stimulation. The surgeon tests the stimulation to maximize symptom suppression and minimize side effects before placement of a permanent stimulation electrode lead. Once the surgeon determines the exact target site of the brain, the temporary stimulation lead is removed and the surgeon commences the process of inserting the permanent stimulation electrode lead (hereinafter "stimulation lead"). Using the stereotactic frame and a hydraulic drive, the stimulation lead is inserted through the burr hole in the patient's skull and implanted in the target site within the brain.

A burr hole lead anchoring device (hereinafter "burr hole device") is then implanted to support and secure the stimulation lead. Burr hole devices are manufactured, for example, by Medtronic, Inc. of Minneapolis, Minn. (the "Medtronic burr hole device") and Image-Guided Neurologics, Inc. of Melbourne, Fla. under the trade name NAVIGUS® (the "IGN burr hole device"). An example of a Medtronic burr hole device is shown and described in U.S. Pat. No. 6,044,304, which is hereby incorporated by reference in its entirety herein. An example of an IGN burr hole device is shown and described in U.S. Patent Publication No. 2002/0052610 published on May 2, 2002, which is hereby incorporated by reference in its entirety herein.

Illustrated in FIGS. 1A-1B is one embodiment of a Medtronic burr hole device 5 includes a burr hole base ring 10 having an upper flange portion 15 and a lower sleeve portion 20 extending from the upper flange portion 15. The base ring 10 also has circumferential ribs 25 disposed about the periphery of the lower sleeve portion 20 and a septum 30 contained within an aperture 35 of the base ring 10. The aperture 35 serves as the opening through which the stimulation lead extends. The base ring 10 may be secured to a skull portion of the brain through a press fit where the circumferential ribs 25 engage the side wall of the burr hole and the septum 30 accepts and secures the stimulation lead in a substantially fixed position relative to the brain. The base ring 10 may include one or more grooves 40 positioned along the upper flange portion 15 of the base ring 10 to accept the stimulation lead. A cap (not shown) may be configured to close the aperture 35 of the burr hole base ring 10, and includes an opening to permit the stimulation lead to exit the base ring 10 via one of the grooves 40 in the base ring 10.

Illustrated in FIG. 2 is one embodiment of a IGN burr hole device 200 that can include a base ring 210, a support clip 215, and a cap 220. The base ring 210 includes a flange portion 225 having an aperture 230 communicating with the burr hole and two mounting holes 235 for attachment to the patient's skull. The base ring 210 may be secured to a skull portion of the brain through the use of two titanium screws 240 inserted through the mounting holes 235 and screwed into the skull. The base ring 210 includes one or more grooves 245 positioned along the upper flange portion 225 of the base ring 210 to receive the stimulation lead and permit the stimulation lead to lie generally parallel to the skull surface. The support clip 215 includes a disk 250 coupled to a cam 255. The cam 255 rotates, with respect to the disk 250, about an axis perpendicular to the plane of the disk 250, to create and substantially close a lead receiving opening 260 in which the stimulation lead is either passed freely (when open) or secured (when closed). The support clip 215 snap-fits onto the base ring 210 in any rotational orientation. The cap 220 includes an opening 265 to permit the stimulation lead to exit the base ring 410 via one of the grooves 245 in the base ring 210 and snap-fits into the base ring 210.

Once the burr hole device is properly implanted, the patient is put under general anesthesia. The connector on the proximal end of the stimulation lead is then connected to the extension lead. The extension lead is passed under the skin of the scalp, neck, and shoulder to connect the stimulation lead to the IPG. Finally, a small incision is made near the clavicle, and the IPG is implanted subcutaneously.

Illustrated in FIGS. 3A-3B are a cross-sectional view and a plan view, respectively, of a stimulation lead L implanted in the brain of a patient using a prior art burr hole device. The stimulation lead L can be described as having three portions as shown in FIGS. 3A-3B: 1) a first portion, which extends from a target site 305 in the patient's brain 310 to the burr hole device 315 in the patient's skull 320, that is typically between about 5 cm to about 12 cm long (indicated as "L1"); 2) a second portion, which extends from approximately the burr hole device 315 in the patient's skull 320 to the extension lead 325 (indicated as "L2"), that is typically between about 5 cm and about 20 cm; and 3) a third portion that is the excess portion of the stimulation lead L (indicated as "L3"). The excess portion of the stimulation lead L can be defined as a length of lead greater than a required length of lead to connect the stimulation lead L to the extension lead, if present, or to the IPG if the extension lead is not present. In other words, the excess portion of the stimulation lead L is the extra slack remaining after the stimulation lead L and the burr hole device have been implanted. In a typical DBS procedure, the excess portion of the stimulation lead L may be as long as about 30 cm long when using the 40 cm stimulation lead or as long as about 13 cm long when using the 28 cm stimulation lead. To manage the excess portion of the stimulation lead L, the surgeon typically inserts the excess portion of the stimulation lead L under the scalp in a random fashion using his/her fingers or a medical instrument.

Likewise, during the surgical procedure, the length of the portion of the extension lead extending from the IPG in the patient to the connection to the stimulation lead L is between about 10 cm to about 51 cm. Therefore, an excess portion of the extension lead exists. The excess portion of the extension lead can be defined as a length of lead greater than a required length of lead to connect the extension lead to the stimulation lead L. To manage the excess portion of the extension lead, the surgeon typically routes the excess portion of the extension lead in a random fashion using his/her fingers or a medical instrument.

The random management of the excess portion of the stimulation lead L and/or the excess portion of the extension lead can present MRI safety concerns to a patient having an implanted neurostimulation system. One possible MRI safety issue that can exist with patients having implanted neurostimulation systems is excessive heating of the electrode contacts on the stimulation lead L when the patient undergoes an MRI procedure. While not wishing to be bound by theory, the mechanism that can be responsible for MRI-related heating of the electrode contacts of the lead L is the electric current induced in the lead wires by the RF and pulsed gradient magnetic fields created by the MRI system. The lead wire can essentially act as an "antenna" and the electric field accompanying the RF and magnetic fields can induce current in the lead wire. A portion of the induced current can pass through the electrode contacts into the surrounding tissue, resulting in heating of the tissue. The RF and pulsed gradient magnetic fields can also induce functional disruption of the operational aspects of the implanted devices.

Other potential concerns that can exist with the random management of the excess portion of the stimulation lead L and/or the excess portion of the extension lead include the absence of a standardized procedure to manage the excess lead and the difficulty in making revision surgery.

BRIEF DESCRIPTION OF THE DRAWINGS

These and other features, aspects, and advantages of the present invention will become better understood with regard to the following description, appended claims, and accompanying drawings where:

FIG. 1B illustrates a perspective view of the device 1100 with lead L in a coiled configuration;

DETAILED DESCRIPTION

Figure 1A:
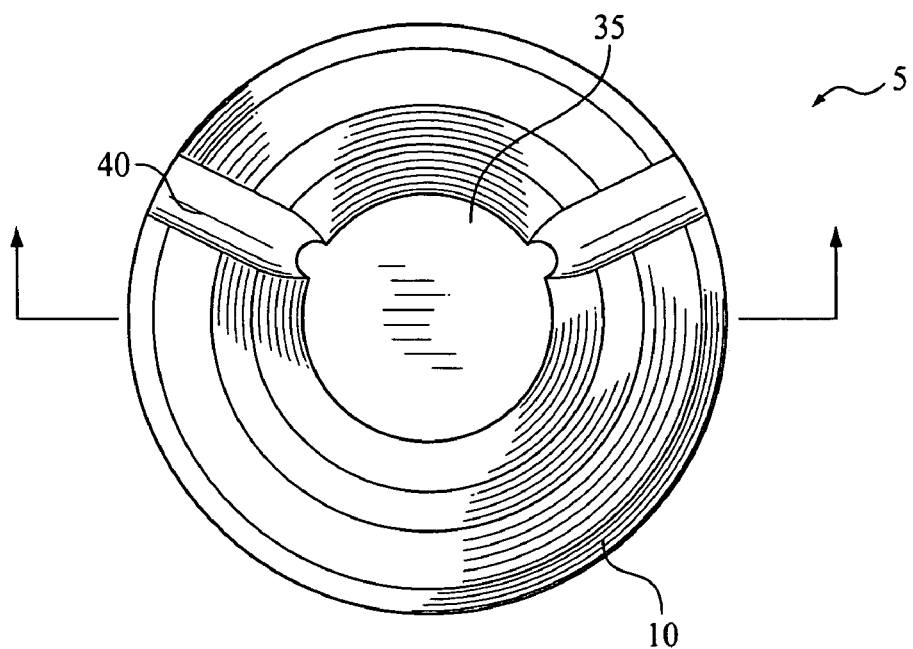
FIG. 1A illustrates a top view of the Medtronic burr hole device base ring 65.
Figure 1B:
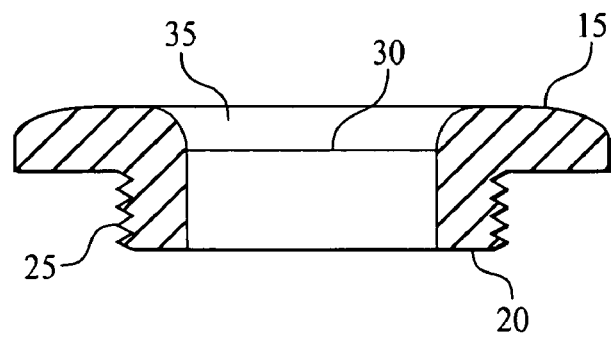
FIG. 1B illustrates a cross-sectional view of FIG. 1A taken along section A-A.
Figure 2:
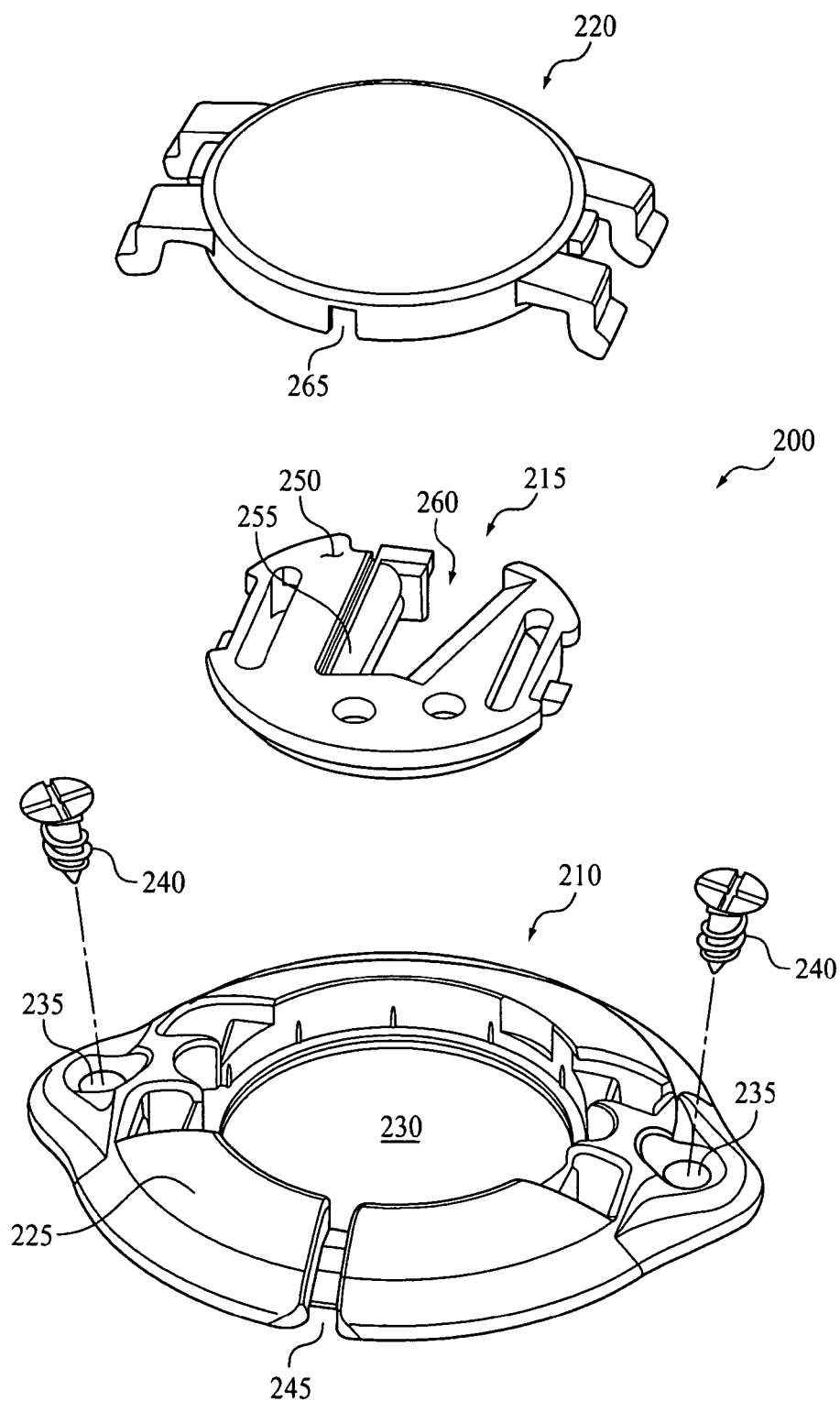
FIG. 2 illustrates an exploded perspective view of the IGN burr hole device 400.
Figure 3A:
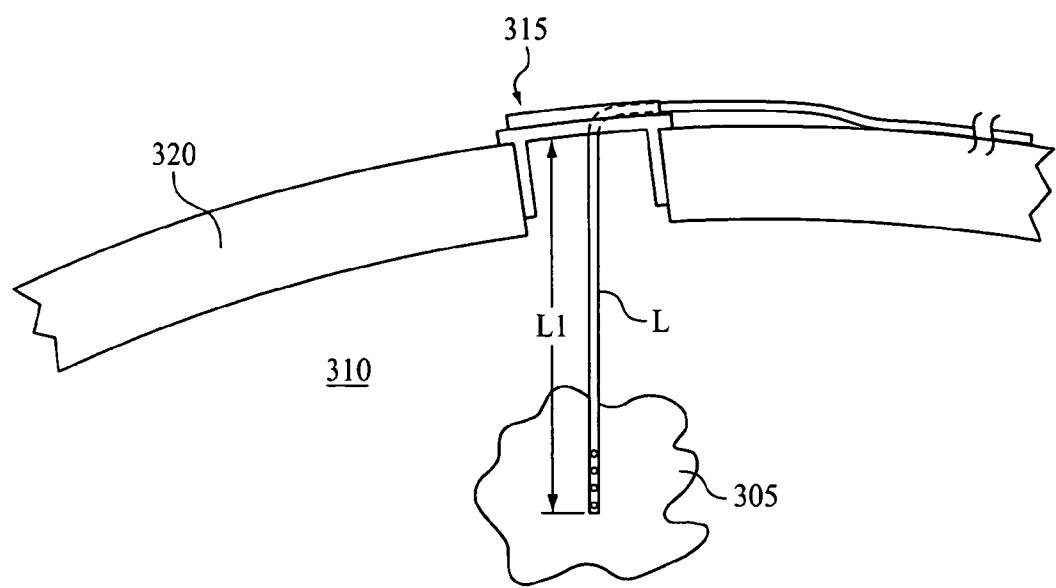
FIG. 3A illustrates a cross-sectional view of a stimulation lead L implanted in the brain of a patient using a prior art burr hole device.
Figure 3B:
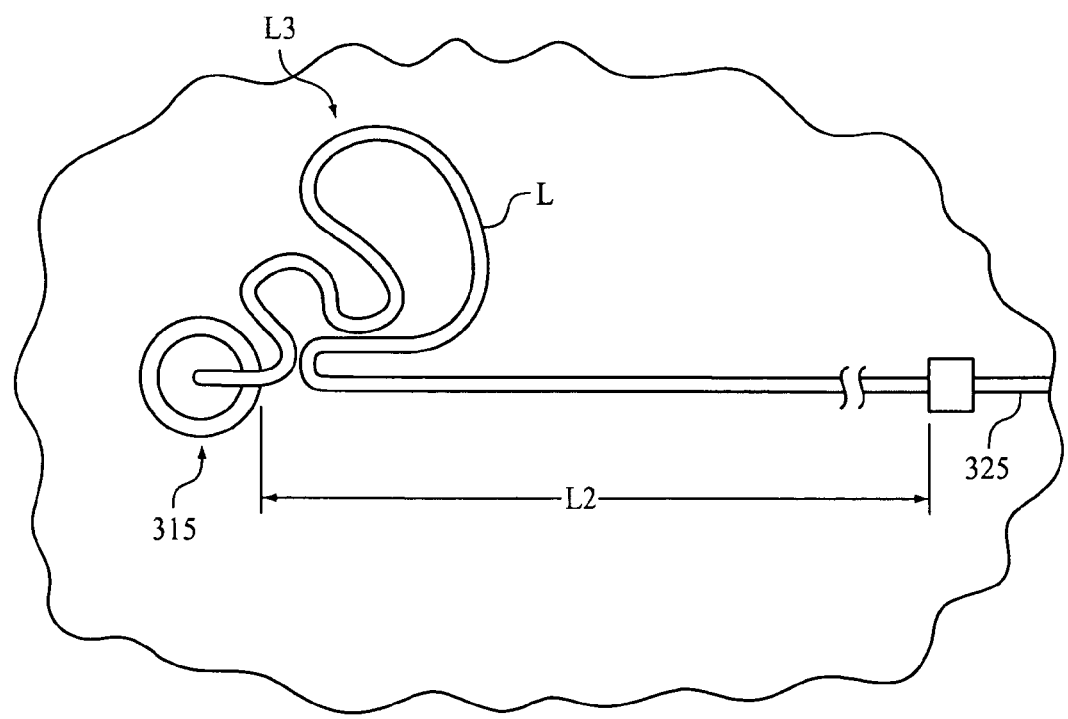
FIG. 3B illustrates a top plan view of a stimulation lead L implanted in the brain of a patient using a prior art burr hole device.

In the description that follows, like parts are indicated throughout the specification and drawings with the same reference numerals, respectively. The figures are not drawn to scale and the proportions of certain parts have been exaggerated for convenience of illustration. It will be appreciated that one element may be designed as multiple elements or that multiple elements may be designed as one element. An element shown as an internal component of another element may be implemented as an external component and vice versa.

Figure 4A:
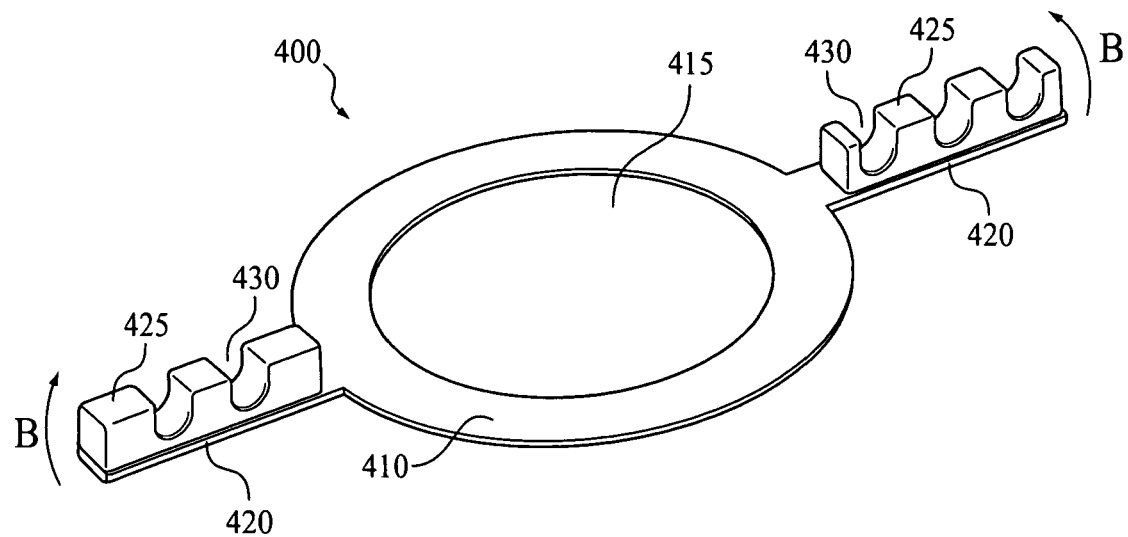
FIG. 4A illustrates a perspective view of one embodiment of a device 400 for retaining an excess portion of a lead implanted in the brain of a patient.
Figure 4B:
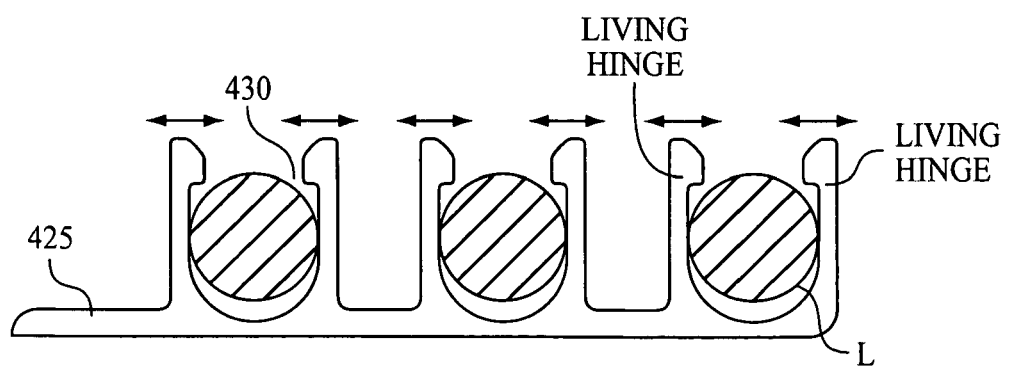
FIG. 4B illustrates a side view of an alternative embodiment of a lead retainer 425 that includes living hinges.
Figure 4C:
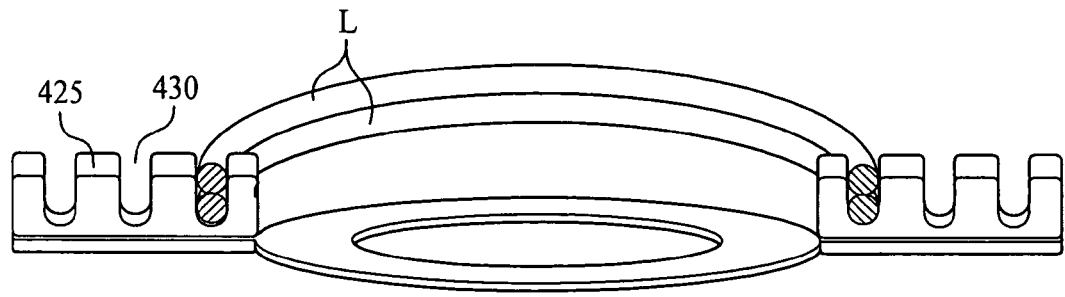
FIG. 4C illustrates a side view of an alternative embodiment of a device for retaining an excess portion of a lead implanted in the brain of a patient having grooves 430 that are deep enough to retain multiple section of the excess portion of the lead L.

Illustrated in FIGS. 4A-4C is one embodiment of a device 400 for retaining an excess portion of a lead that is implanted in or on a surface of a brain of a patient. The device 400 can be used by itself or in conjunction with the Medtronic burr hole device, the IGN burr hole device, or any other commercially available burr hole device.

The device 400 includes a disk 410 having an aperture 415 disposed therein for receiving a lead L. In one embodiment, the aperture 415 in the disk 410 can be dimensioned to receive a lower sleeve portion of a Medtronic and/or other commercially available burr hole device having a lower sleeve portion. In another embodiment, the device 400 can be used in conjunction with the IGN or other commercially available burr hole device not having a lower sleeve portion. In this embodiment, the device 400 can be positioned between the burr hole device and a surface of the skull in a manner such that the aperture 415 of the device 400 can be generally aligned with the aperture in the burr hole device and the burr hole. In yet another embodiment, the device 10 can be used by itself as a burr hole ring and secured to the a surface of the skull in a manner such that the aperture 415 of the device 400 can be generally aligned with the burr hole. In this embodiment, a burr hole cap (not shown) can be used to close the aperture 415 and anchor the lead L in place.

It will be appreciated that the disk 410 can be made in various sizes and shapes of the disk 410. The selection of the size and/or shape of the disk 410 can depend on numerous factors such as the size or shape of the burr hole, the size or shape of the incision, the manner in which the burr hole ring is to be secured to the skull, etc.

In one embodiment, the disk 410 can include tabs or substrate 420 that extend radially outward therefrom. Each tab 420 can include a lead retainer 425 for storing at least a section of the excess portion of the lead L. The lead retainers 425 may be affixed to the tabs 420 by an adhesive bond using a suitable biocompatible adhesive or may be affixed to the tabs 420 by other attachment means such as screws, snaps, or combinations of attachment devices. In one embodiment, the height of the lead retainers 425 can be configured such that they do not extend beyond the height of the burr hole device cap.

In one embodiment, the lead retainers 425 each include one or more grooves 430 disposed therein for storing at least a section of the excess portion of the lead L. The device 400 can be configured with any number of desired grooves in each lead retainer 425. It will be appreciated that the number of grooves 430 in one lead retainer 425 may differ from the number of grooves 430 in another lead retainer 425 or there may be the same number of grooves 430 in each lead retainer 425.

In one embodiment, the width of each groove 430 can be less than an outside diameter of the lead L, but configured to accept the lead L by increasing the width of the groove 430 a distance at least as great as the outside diameter of the lead L when a force is being applied to insert the lead L into the groove 430. When the force is released, the width of the groove 430 is reduced to retain the lead L. In another embodiment, the grooves 430 may be provided in between living hinges as shown in FIG. 4B. In this embodiment, the width of each groove 430 may be enlarged to accept the outside diameter of the lead L.

In one embodiment, the depth of each groove 430 can be deep enough to retain one section of the excess portion of the lead L. In another embodiment, the depth or each groove 430 can be deep enough to retain multiple sections of the excess portion of the lead L as shown in FIG. 4C.

In one embodiment, the disk 410 can be constructed of a thin, flexible material such that the tabs 420 may be folded inward in a direction indicated by arrows B so that the device 400 may be inserted through a relatively small surgical incision in the scalp. Examples of suitable materials include polyurethane, silicone rubber, and biocompatible elastomers. The lead retainers 425 may be constructed of a less resilient material such as polycarbonate, polypropylene, polyethylene, or nylon.

Although FIG. 4 illustrates that the disk 410 and the tabs 420 are one part and the lead retainers 425 are separate parts, it will be appreciated that the disk 410, the tabs 420, and the lead retainers 425 may be unitary in construction. Accordingly, the lead retainers 425 may be constructed from the same material as the disk 410.

It will be appreciated that the device 400 can include any desired number of lead retainers 425 extending from the disk. Additionally, although the lead retainers 425 illustrated in the figures are oriented 180 degrees from each other, it will be appreciated that the lead retainers 425 may be oriented in an angular position relative to each other. Further, if more than two lead retainers 425 are provided, each lead retainer 425 may be spaced apart from each other at any angular position.

In another embodiment, the disk 410 and the extended tabs 420 may be constructed of a stiffer, more rigid material. In this embodiment, the tabs 420 can be foldable with respect to the disk 415 via a living hinge provided between the tabs 420 and the disk 410. In this embodiment, the disk 410 and the extended tabs 420 may be constructed from metal so that the device 400 may be made thinner than plastic or elastomer versions.

Figure 4D:
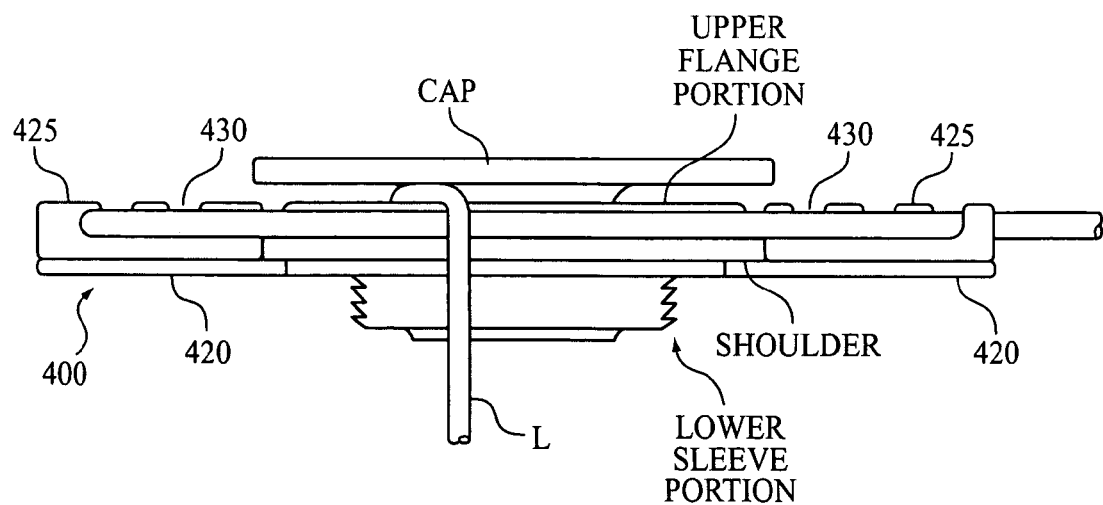
FIG. 4D illustrates a side view of the device 10 used in conjunction with a prior art burr hole device.

In an example operation, a burr hole (circular or other shape) is first drilled in the skull of the patient to gain access to the patient's brain. One end of the lead L can then be implanted in a target site of the patient's brain. The device 400 can then be threaded over the lead L through the aperture 415. Then, the tabs 420 may be folded inward to allow a surgeon to insert the device 400 through the surgical incision. The device 400 can then be centered over the burr hole. If using the device 400 in conjunction with the Medtronic burr hole device or any other commercially available burr hole device having a lower sleeve portion, the burr hole ring can be implanted by pressing the lower sleeve portion into the burr hole until the device 400 is seated between the shoulder (the lower surface of the upper flange portion) and the outer surface of the skull to secure the device 400 as shown in FIG. 4D. If using the device 400 in conjunction with the IGN burr hole device or any other commercially available burr hole device not having a lower sleeve portion, the base ring of such burr hole device can be screwed into the skull to secure the base ring and the device 400. If the device is used by itself, the device 400 can be secured to the skull using screws or any other attachment means.

Figure 4E:
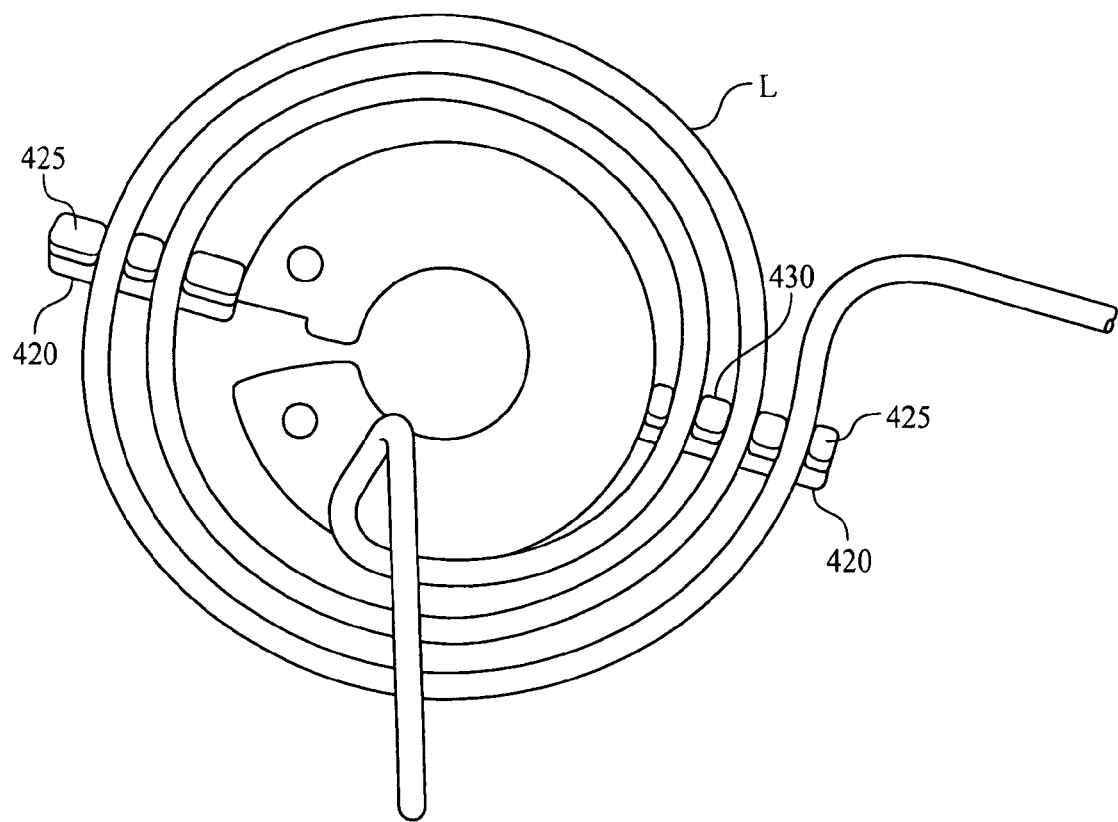
FIG. 4E illustrates a perspective view of the device 10 used in conjunction with a prior art burr hole device where the lead L is routed in a coiled configuration.

Once the device 400 is implanted, the tabs 420 can be folded outward to permit the surgeon to begin retaining any of the excess portion of the lead L. As shown in FIG. 4E, the surgeon can insert multiple sections of the excess portion of the lead L into the grooves 430 in the lead retainers 425 to form a coil or spiral around the burr hole until all of the excess portion of the lead L is used up.

Figure 5A:
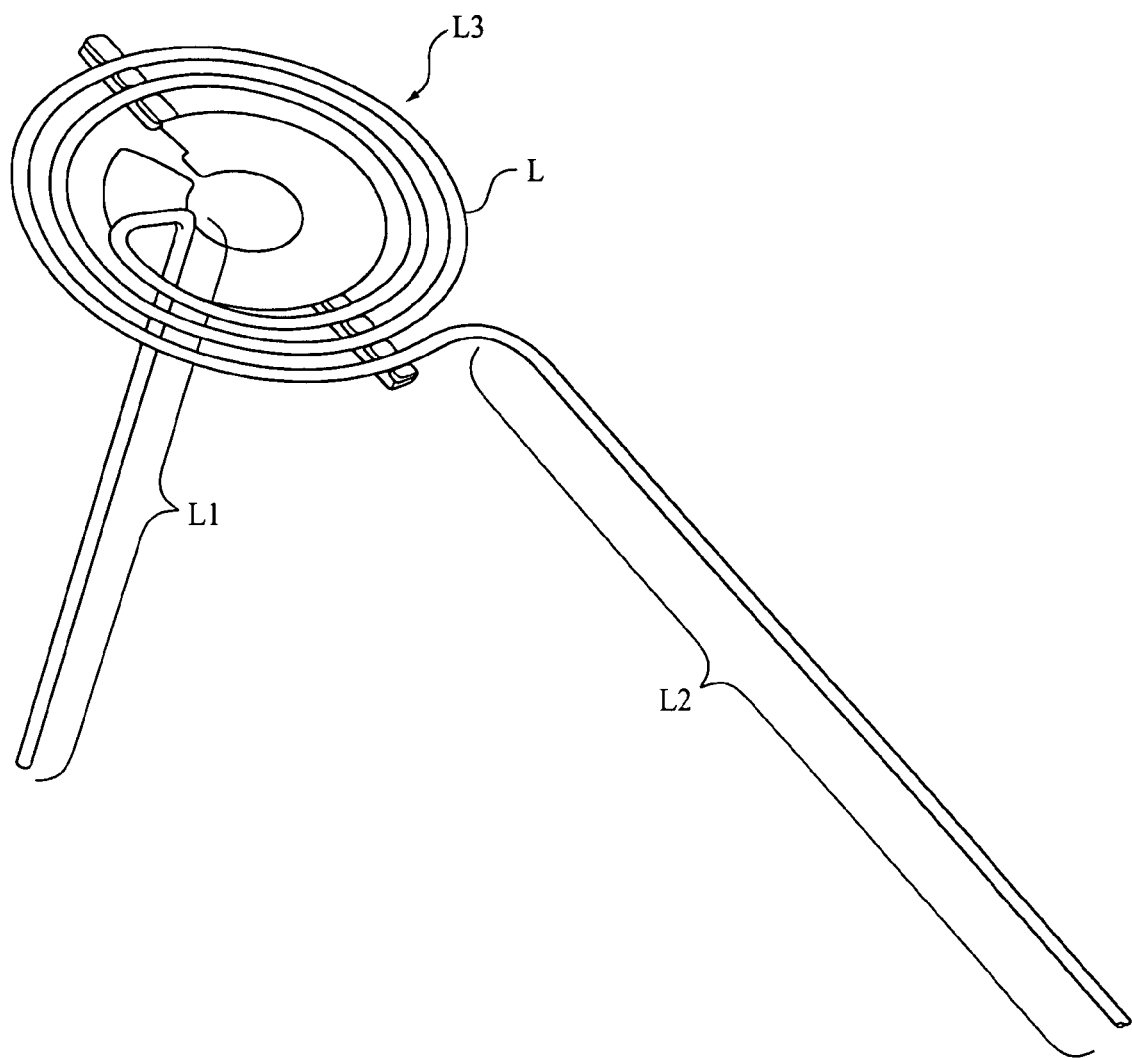
FIG. 5A illustrates a perspective view of the excess lead management device 10 inserted on base ring 65 with stimulation lead L in a coiled configuration.

Illustrated in FIG. 5A is a perspective view of the device 400 with the excess portion of the lead L in a coiled configuration. The lead L can be described as having three portions as shown in FIG. 5A: 1) a first portion that extends from the target site in the patient's brain to the burr hole device in the patient's skull (indicated as "L1"); 2) a second portion that extends from the burr hole device in the patient's skull to the extension lead (indicated as "L2"), and 3) a third portion that is the excess portion of the lead L (indicated as "L3"). As shown in FIG. 5A, the excess portion of the lead L3 is coiled around the burr hole in a counterclockwise fashion, but may, however, be coiled in a clockwise fashion.

Figure 5B:
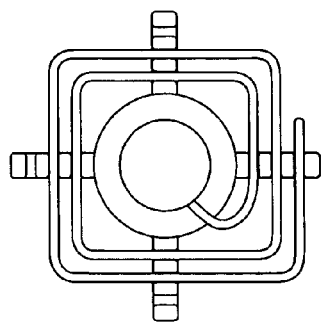
FIG. 5B-5F illustrate various top views of coiling configurations.
Figure 5C:
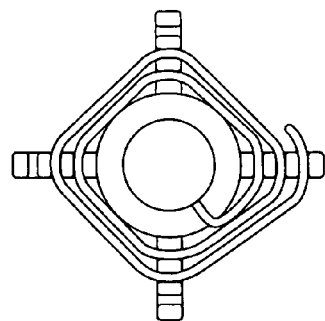
Figure 5D:
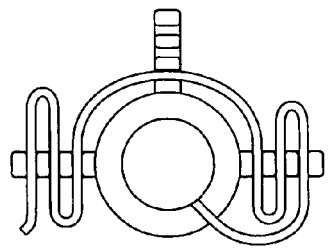
Figure 5E:
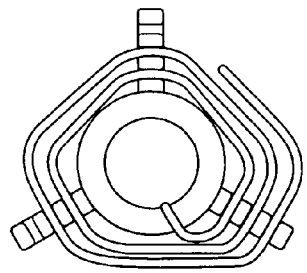
Figure 5F:
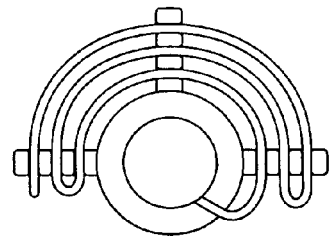

Further, for illustration purposes only, FIG. 5A depicts that the coiling configuration of the excess portion of the lead L results in a circular coil around the burr hole. However, in reality, the coiling configuration of the devices discussed herein may take the form of any shape and need not loop completely around the burr hole. Examples of other shapes are illustrated in FIGS. 5B-5F where FIG. 5B illustrates a rectangular shaped coil (shown with four extended tabs), FIG. 5C illustrates a diamond shaped coil (shown with four extended tabs), FIG. 5D illustrates a wave shaped coil (shown with three extended tabs), FIG. 5E illustrates a pentagonal shaped coil (shown with three extended tabs), and FIG. 5F illustrates a semi-circular shaped coil (shown with three extended tabs).

In one embodiment, the excess portion of the lead L can be formed into a coiling configuration that can satisfy at least one MRI safety concern. For example, a coiling configuration can reduce a change in temperature at electrical contacts of the lead L when the patient is undergoing an MRI procedure or subjected to an otherwise substantial electromagnetic field. In one embodiment, the heating of the electrode contacts, while the patient is undergoing an MRI procedure or subjected to an otherwise substantial electromagnetic field, can be minimized by configuring the excess portion of the lead L into one or more loops. While not wishing to be bound by theory, the formation of the excess portion of the lead L into loops can minimize this "antenna" effect and, thus, minimize excessive heating of the electrode contacts. In one embodiment, the change in temperature at the electrodes decreases as the number of loops of the excess portion of the lead L increases.

Figure 6A:
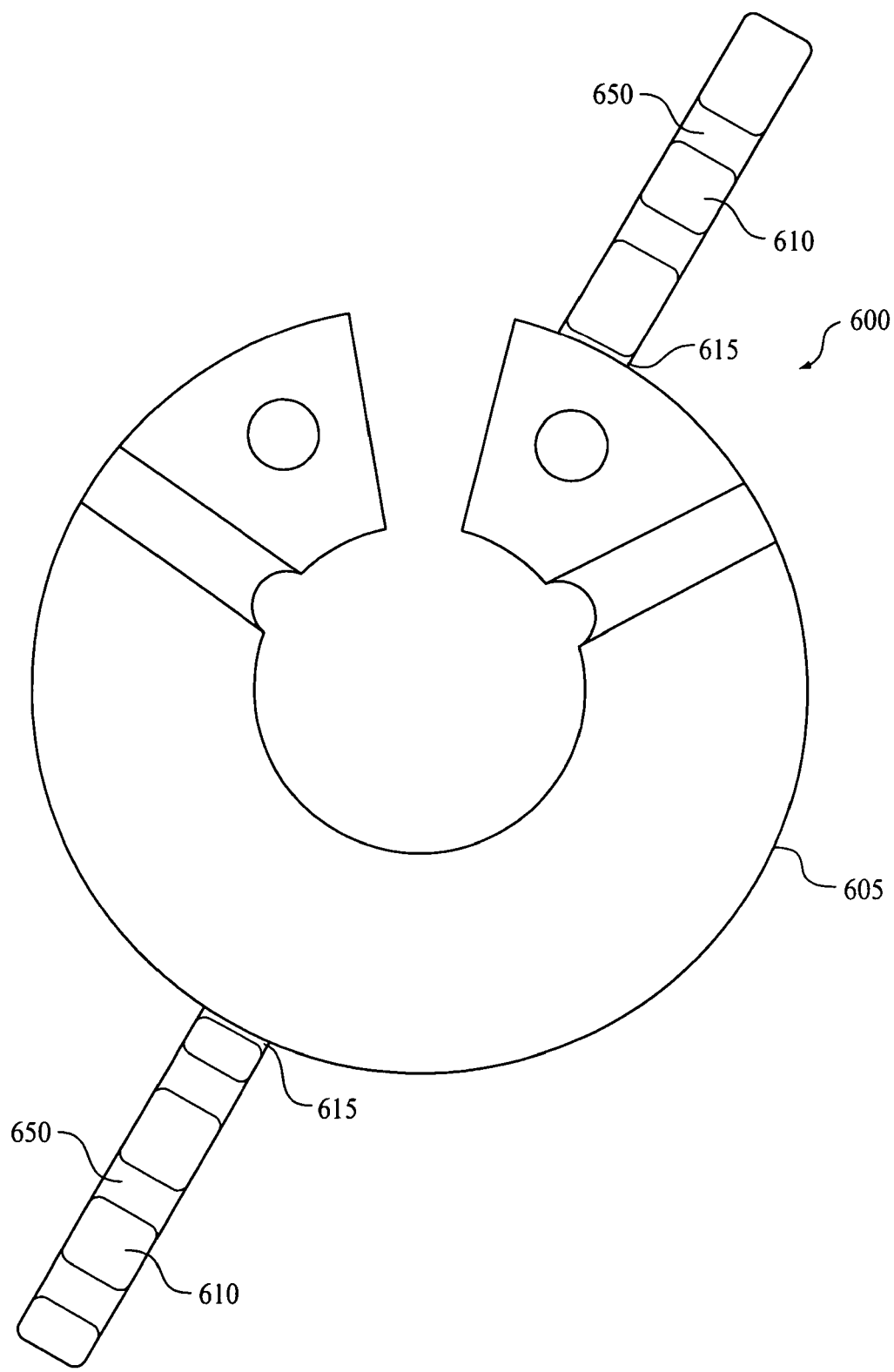
FIG. 6A illustrates a top view of another embodiment of a device 600 for retaining an excess portion of a lead implanted in the brain of a patient.
Figure 6B:
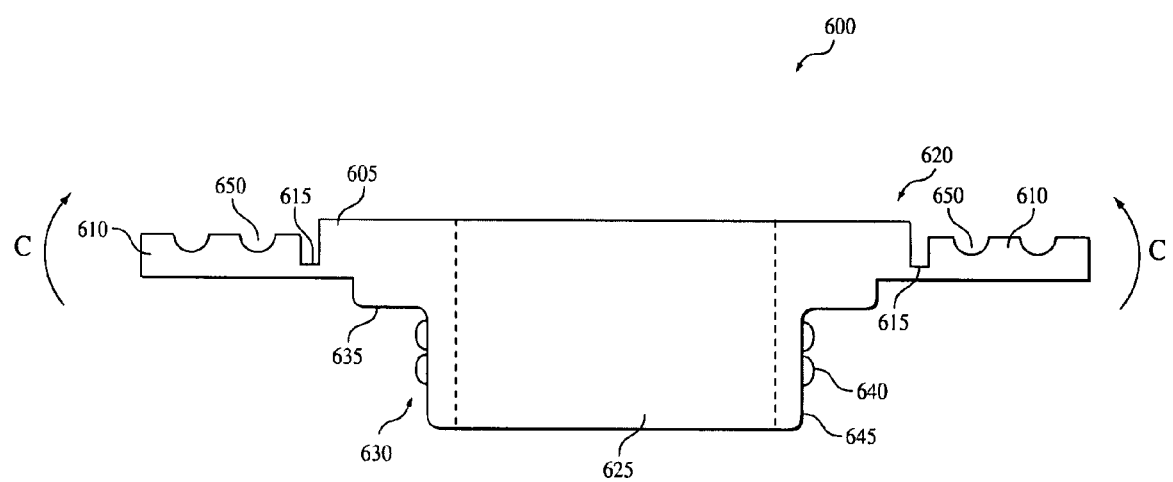
FIG. 6B illustrates a side view of the device 600 as shown in FIG. 6A.

Illustrated in FIGS. 6A-6B is another embodiment of a device 600 for retaining the excess portion of a lead implanted in or on a surface of the brain of a patient. The device 600 includes a burr hole ring 605 having lead retainers 610 that can extend radially outward from the burr hole ring 605. The lead retainers 610 are configured to store at least a section of the excess portion of the lead L. In one embodiment, the lead retainers 610 can be foldable with respect to the burr hole ring 605 via living hinges 615 provided between the lead retainers 610 and the burr hole ring 605. For example, each lead retainer 610 can be movable in the direction indicated by arrow C with respect to the burr hole ring 605 between an expanded position (illustrated in FIGS. 6A-6B) and a collapsed position (not shown) to permit the device to be inserted through an incision in a scalp of the patient when the lead retainer is moved in the collapsed position.

It will be appreciated that there are many possible sizes and shapes of burr hole rings. The selection of one burr ring over another can depend on numerous factors such as the size or shape of the burr hole, the size or shape of the incision, the manner in which the burr hole ring is to be secured to the skull, etc. Thus, it should be understood that the following description, by way of example, illustrates exemplary burr hole ring configurations which may be used in connection with the present invention.

In one embodiment, the burr hole ring 605 can include a sleeve portion 620 having a central lumen 625 and a flange portion 630 extending from one end of the sleeve portion 620 forming a shoulder 635 as shown in FIG. 6B. The sleeve portion 620 can include circumferential ribs 640 on an outside surface 645 of the sleeve portion 620. In another embodiment not illustrated in the figures, the burr hole ring 605 can include a disk having an aperture disposed therein (e.g., a ring) and does not include a sleeve portion. Thus, as used herein, the term "burr hole ring" can refer to a simple ring-shaped member or a more complex structure that includes a sleeve.

In one embodiment, the lead retainers 610 each include one or more grooves 650 disposed therein for storing at least a section of the excess portion of the lead L. The device 600 can be configured with any number of desired grooves in each lead retainer 610. It will be appreciated that the number of grooves 650 in one lead retainer 610 may differ from the number of grooves 650 in another lead retainer 610 or there may be the same number of grooves 650 in each lead retainer 610.

In one embodiment, the width of each groove 650 can be less than an outside diameter of the lead L, but configured to accept the lead L by increasing the width of the groove 650 a distance at least as great as the outside diameter of the lead L when a force is being applied to insert the lead L into the groove 650. When the force is released, the width of the groove 650 is reduced to retain the lead L. In another embodiment, the grooves 650 may be provided in between living hinges as shown and described above. In this embodiment, the width of each groove 650 may be enlarged to accept the outside diameter of the lead L.

In one embodiment, the depth of each groove 650 can be deep enough to retain one section of the excess portion of the lead L. In another embodiment, the depth or each groove 650 can be deep enough to retain multiple sections of the excess portion of the lead L as shown and described above.

Although FIGS. 6A-6B illustrate that the lead retainers 610 are formed as an integral portion of the burr hole ring 605, it will be appreciated that the lead retainers 610 may be formed as a part separate and detachable from the burr hole ring 605. Accordingly, the lead retainers 610 and the burr hole ring 605 may be constructed from different materials if desired. In one embodiment, the height of the lead retainers 610 can be configured such that they do not extend beyond the height of the burr hole device cap (not shown).

It will be appreciated that the device 600 can include any desired number of lead retainers 610 extending from the disk. Additionally, although the lead retainers 610 illustrated in the figures are oriented 180 degrees from each other, it will be appreciated that the lead retainers 610 may be oriented in an angular position relative to each other. Further, if more than two lead retainers 610 are provided, each lead retainer 610 may be spaced apart from each other at any angular position.

In another related embodiment, the burr hole ring may be constructed without living hinges between the lead retainers and the burr hole ring. For example, the lead retainers could be configured to resist bending relative to the burr hole ring or the lead retainers could be configured to otherwise reduce the effective diameter of the device to ease installation.

In an example operation, a burr hole is first drilled in the skull of the patient to gain access to the patient's brain. One end of the lead L can then be implanted in a target site of the patient's brain. The device 600 can then be threaded over the lead L through the central lumen 625 of the burr hole ring 605. The lead retainers 610 may be folded inward (if living hinges 615 are present), in the direction as indicated by arrows C, to allow the device 600 to fit through the surgical incision. The device 600 can then be implanted over/into the burr hole in the manner as described above depending on which type of burr hole ring is utilized. Once the device is implanted, the lead retainers can be folded outward (if living hinges 615 are present) to permit the surgeon to begin retaining the excess portion of the lead L. The surgeon can then insert one or more sections of the excess portion of the lead L into one or more grooves 650 in the same manner as shown and described above to form one or more loops.

In one embodiment, the excess portion of the lead L can be formed into a coiling configuration that can satisfy at least one MRI safety concern. For example, a coiling configuration can reduce a change in temperature at electrical contacts of the lead L when the patient is undergoing an MRI procedure or subjected to an otherwise substantial electromagnetic field. In one embodiment, the heating of the electrode contacts, while the patient is undergoing an MRI procedure or subjected to an otherwise substantial electromagnetic field, can be minimized by configuring the excess portion of the lead L into one or more loops. While not wishing to be bound by theory, shortening the effective length of the lead L can reduce this "antenna" effect or arranging the lead L in a particular configuration can cause induced signals to create disruptive interference. In either case, excessive heating of the electrode contacts can be minimized. In one embodiment, the change in temperature at the electrodes decreases as the number of loops of the excess portion of the lead L increases.

Figure 7:
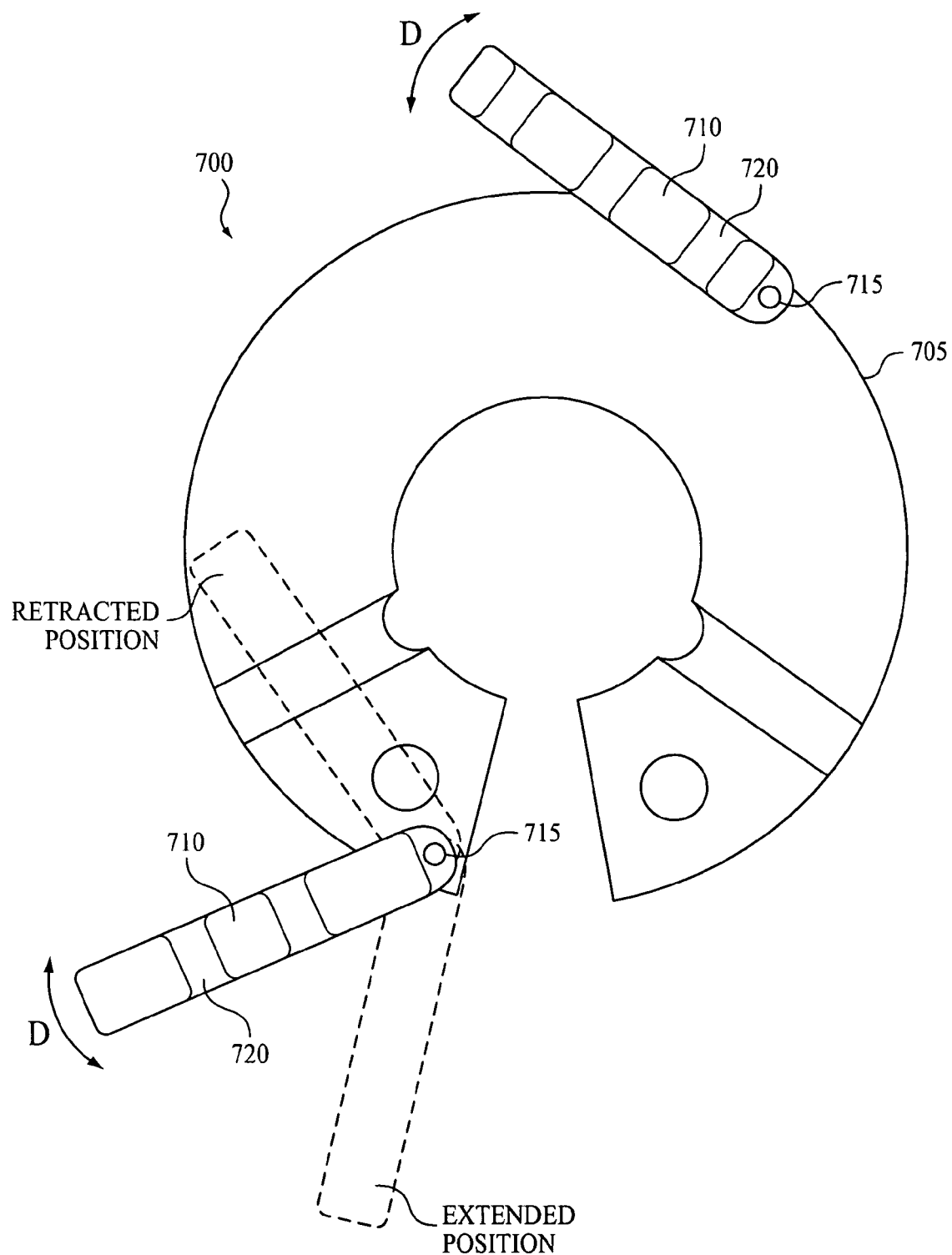
FIG. 7 illustrates a top view of another embodiment of a device 700 for retaining an excess portion of a lead implanted in the brain of a patient.

Illustrated in FIG. 7 is another embodiment of a device 700 for retaining the excess portion of a lead implanted in or on a surface of a brain of a patient. The device 700 includes a burr hole ring 705 having lead retainers 710 that can be configured to be extendable radially outward from the burr hole ring 705. In one embodiment, the lead retainers 710 can be movable with respect to the burr hole ring 705 via a pivotal connection 715 between the lead retainers 710 and the burr hole ring 705. For example, each lead retainer 710 is independently movable in the direction indicated by arrow D with respect to the burr hole ring 705 between an extended position (illustrated in FIG. 7) and a retracted position (not shown) to permit the device to be inserted through an incision in a scalp of the patient when the lead retainer is moved in the collapsed position. The lead retainers 710 can include, for example, a locking mechanism such as a step, snap, or cam to maintain the lead retainers 710 in the extended position.

In one embodiment, the lead retainers 710 can be oriented in a configuration to anchor the lead L. For example, the lead retainers 710 can be operated as "jaws" that are configured to trap or lockingly clamp the lead L therebetween.

In one embodiment, the lead retainers 710 each include one or more grooves 720 disposed therein for storing at least a section of the excess portion of the lead L. The device 700 can be configured with any number of desired grooves in each lead retainer 710. It will be appreciated that the number of grooves 720 in one lead retainer 710 may differ from the number of grooves 720 in another lead retainer 710 or there may be the same number of grooves 720 in each lead retainer 710.

In one embodiment, the width of each groove 720 can be less than an outside diameter of the lead L, but configured to accept the lead L by increasing the width of the groove 720 a distance at least as great as the outside diameter of the lead L when a force is being applied to insert the lead L into the groove 720. When the force is released, the width of the groove 720 is reduced to retain the lead L. In another embodiment, the grooves 720 may be provided in between living hinges as shown and described above. In this embodiment, the width of each groove 720 may be enlarged to accept the outside diameter of the lead L.

In one embodiment, the depth of each groove 720 can be deep enough to retain one section of the excess portion of the lead L. In another embodiment, the depth or each groove 720 can be deep enough to retain multiple sections of the excess portion of the lead L as shown and described above.

Although FIG. 7 illustrates that the lead retainers 710 are formed as an integral portion of the burr hole ring 705, it will be appreciated that the lead retainers 710 may be formed as a part separate and detachable from the burr hole ring 705. Accordingly, the lead retainers 710 and the burr hole ring 705 may be constructed from different materials if desired. In one embodiment, the height of the lead retainers 710 can be configured such that they do not extend beyond the height of the burr hole device cap (not shown).

It will be appreciated that the device 700 can include any desired number of lead retainers 710 extending from the burr hole ring 705. Additionally, although the lead retainers 710 illustrated in the figures are disposed on opposing sides of the burr hole ring 705, it will be appreciated that the lead retainers 710 may be oriented in an angular position relative to each other. Further, if more than two lead retainers 710 are provided, each lead retainer 710 may be spaced apart from each other at any angular position.

In an example operation, a burr hole is first drilled in the skull of the patient to gain access to the patient's brain. One end of the lead L can then be implanted in a target site of the patient's brain. The device 700 can then be placed around the lead L. The lead retainers 710 may be swung inward to the retracted position to allow the device 700 to fit through the surgical incision. The device 700 can then be implanted over/into the burr hole in the manner as described above depending on which type of burr hole device is modified. Once the device 700 is implanted, the lead retainers can be folded outward to the retracted position to permit the surgeon to begin retaining the excess portion of the lead L. The surgeon can then insert one or more sections of the excess portion of the lead L into one or more grooves 720 in the same manner as shown and described above to form one or more loops.

In one embodiment, the excess portion of the lead L can be formed into a coiling configuration. For example, a coiling configuration can reduce a change in temperature at electrical contacts of the lead L when the patient is undergoing an MRI procedure or subjected to an otherwise substantial electromagnetic field. In one embodiment, the heating of the electrode contacts, while the patient is undergoing an MRI procedure or subjected to an otherwise substantial electromagnetic field, can be minimized by configuring the excess portion of the lead L into one or more loops. While not wishing to be bound by theory, particular arrangements of the excess portion of the lead L, such as circles, spirals, or looping, can minimize this "antenna" effect and, thus, minimize undesirable attributes.

Figure 8A:
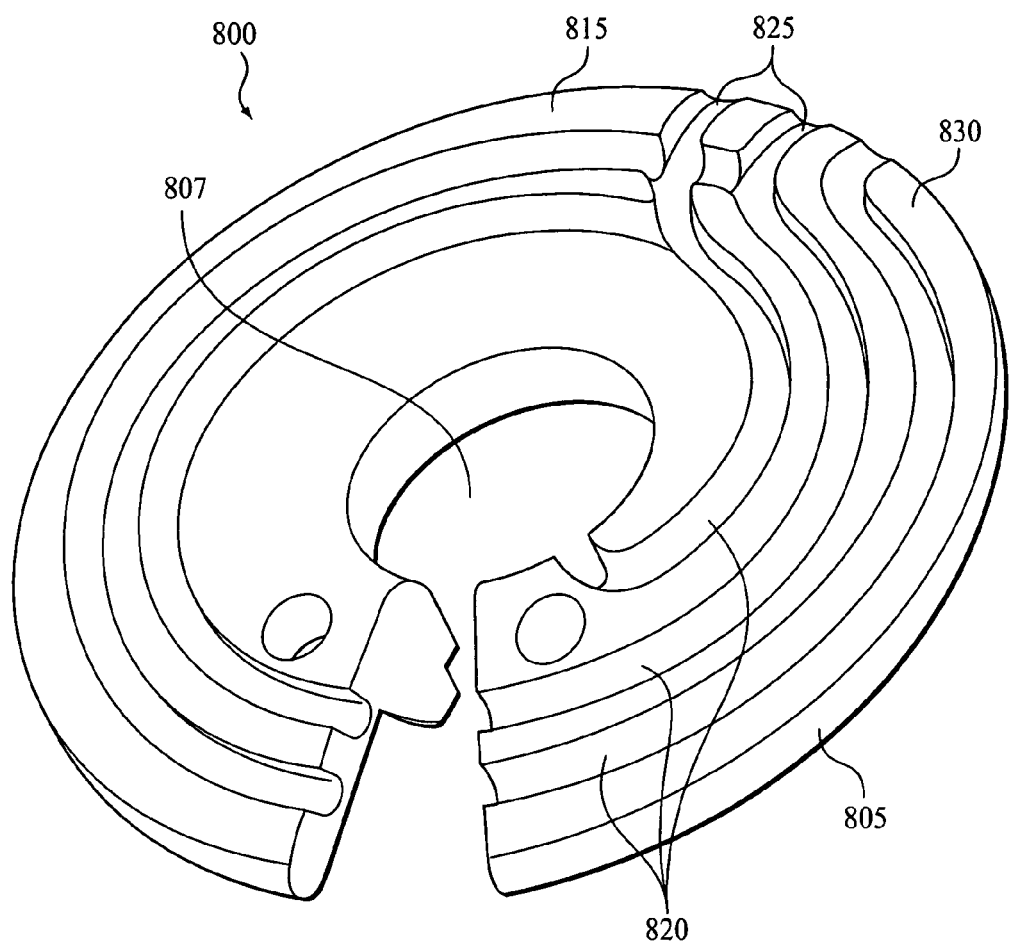
FIG. 8A illustrates a top perspective view of another embodiment of a device 800 for retaining an excess portion of a lead implanted in the brain of a patient.
Figure 8B:
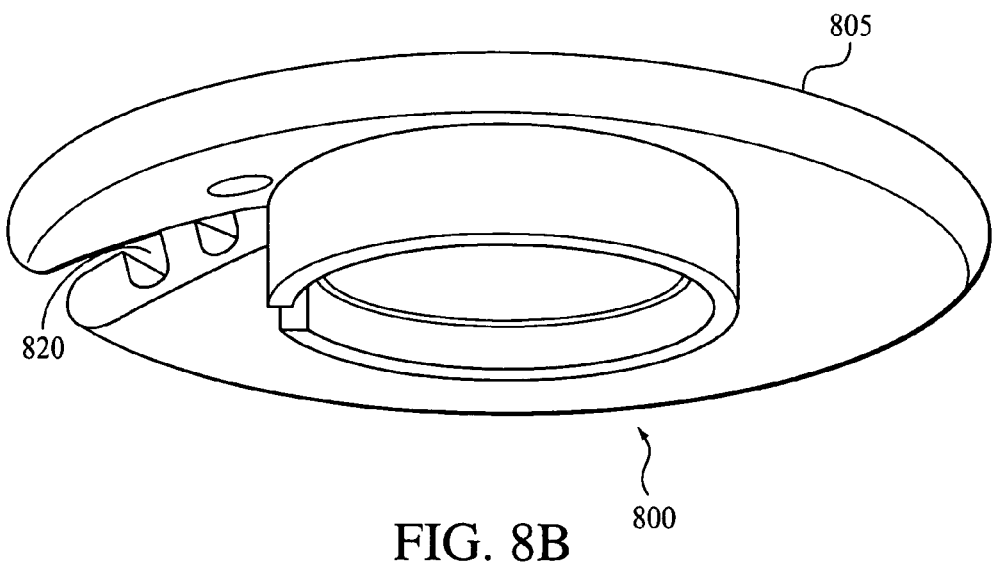
FIG. 8B illustrates a bottom perspective view of the device 800.
Figure 8C:
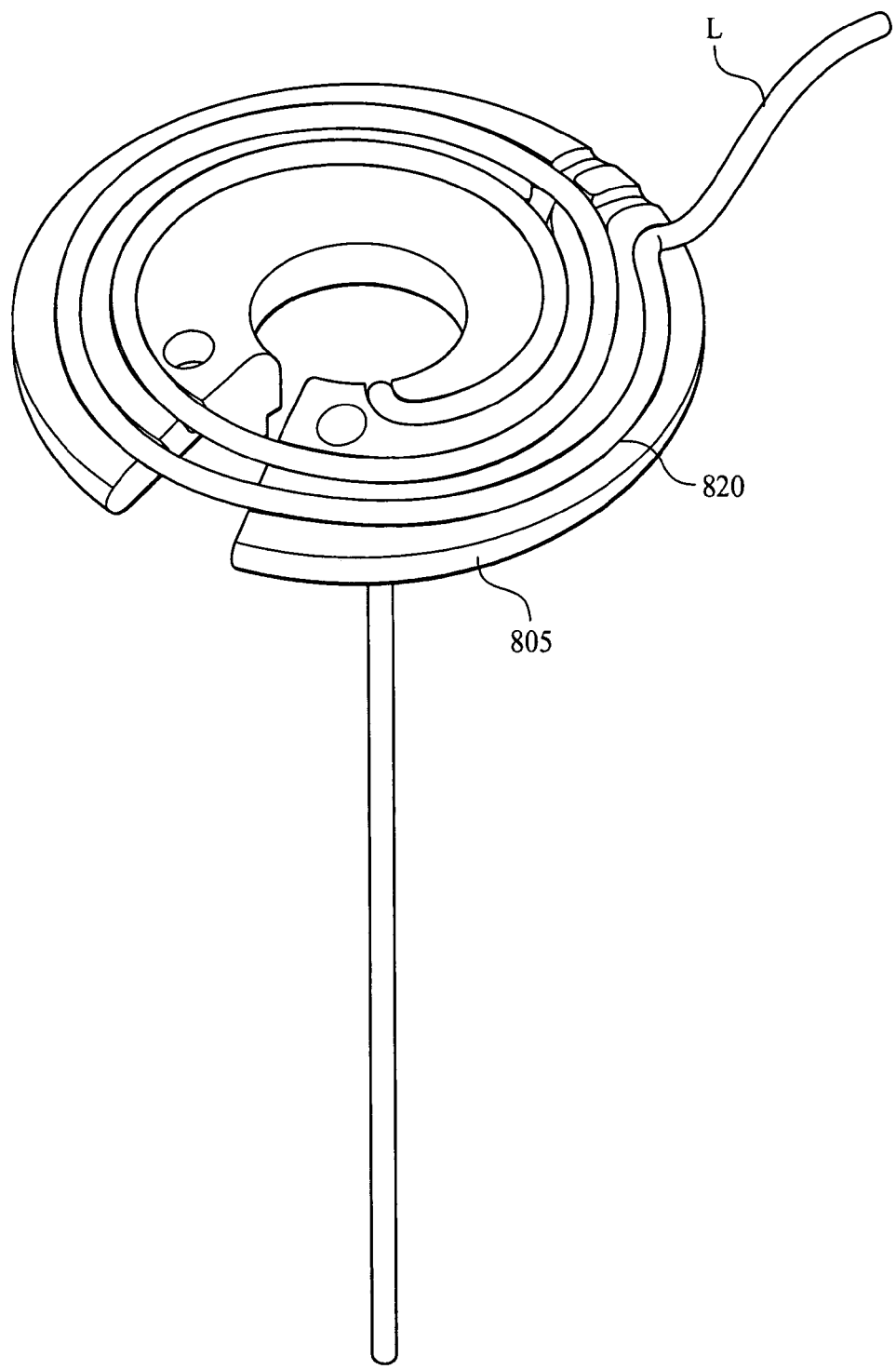
FIG. 8C illustrates a perspective view of the device 800 with lead L in a coiled configuration.

Illustrated in FIGS. 8A-8C is another embodiment of device 800 for retaining at least a section of the excess portion of a lead implanted in or on a surface of a brain of a patient. In this embodiment, the device 800 includes a burr hole ring 805 having an aperture 807 and a lead retainer 810 provided on an outside surface or substrate 815 of the burr hole ring 805 for retaining at least a section of the excess portion of the lead L. Optionally, the diameter of the burr hole ring 805 can be increased to accommodate the lead retainer 810.

In one embodiment, the lead retainer 810 can include a system of grooves 820 disposed in the outside surface 815 of the burr hole ring 805 for retaining at least a section of the excess portion of the lead L. As shown in FIGS. 8A-8C, the system of grooves 820 can include a spiral groove that extends from the aperture 807 to multiple outlet grooves 825 at a periphery 830 of the outside surface 815 of the burr hole ring 805 such that the excess portion of the lead L can be stored in multiple loops in the groove system. It will be appreciated that the excess portion of the lead can be stored in one loop or a partial loop in the groove system.

In one embodiment, the width of each groove 820 can be less than an outside diameter of the lead L, but configured to accept the lead L by increasing the width of the groove 820 a distance at least as great as the outside diameter of the lead L when a force is being applied to insert the lead L into each groove 820. When the force is released, the width of the groove 820 is reduced to retain the lead L. In another embodiment, the grooves 820 may be provided in between living hinges as shown and described above. In this embodiment, the width of each groove 820 may be enlarged to accept the outside diameter of the lead L. In yet another embodiment, the lead L may be retained in the groove 820 by a cap or cover configured to fit over the bur hole ring 805.

In another embodiment, the system of grooves 820 can include a plurality of concentric, grooves extending circumferentially around the outside surface of the burr hole ring, and at least one radially extending groove in the outside surface communicating therewith and extending to an outlet at a periphery of the outside surface of the burr hole ring. Optionally, in another embodiment, the burr hole ring 805 may include tabs (not shown) extending therefrom to form grooves (not shown) therebetween for receiving the excess portion of the lead L.

In an example operation, a burr hole is first drilled in the skull of the patient to gain access to the patient's brain. One end of the lead L can then be implanted in a target site of the patient's brain. The lead L can be passed through the aperture 807 and manipulated to fit through the surgical incision. The device 800 can then be implanted over/into the burr hole in the manner as described above depending on which type of burr hole ring is utilized. Once the device is implanted, the surgeon can begin retaining the excess portion of the lead L. The surgeon can insert one or more sections of the excess portion of the lead L into the system of grooves 820 in the same manner as shown and described above to form one or more loops (see FIG. 8C).

In one embodiment, the excess portion of the lead L can be formed into a coiling configuration that can satisfy at least one MRI safety concern. For example, a coiling configuration can reduce a change in temperature at electrical contacts of the lead L when the patient is undergoing an MRI procedure or subjected to an otherwise substantial electromagnetic field. In one embodiment, the heating of the electrode contacts, while the patient is undergoing an MRI procedure or subjected to an otherwise substantial electromagnetic field, can be minimized by configuring the excess portion of the lead L into one or more loops. While not wishing to be bound by theory, the formation of the excess portion of the lead L into loops can minimize this "antenna" effect and, thus, minimize excessive heating of the electrode contacts. In one embodiment, the change in temperature at the electrodes decreases as the number of loops of the excess portion of the lead L increases.

Figure 9:
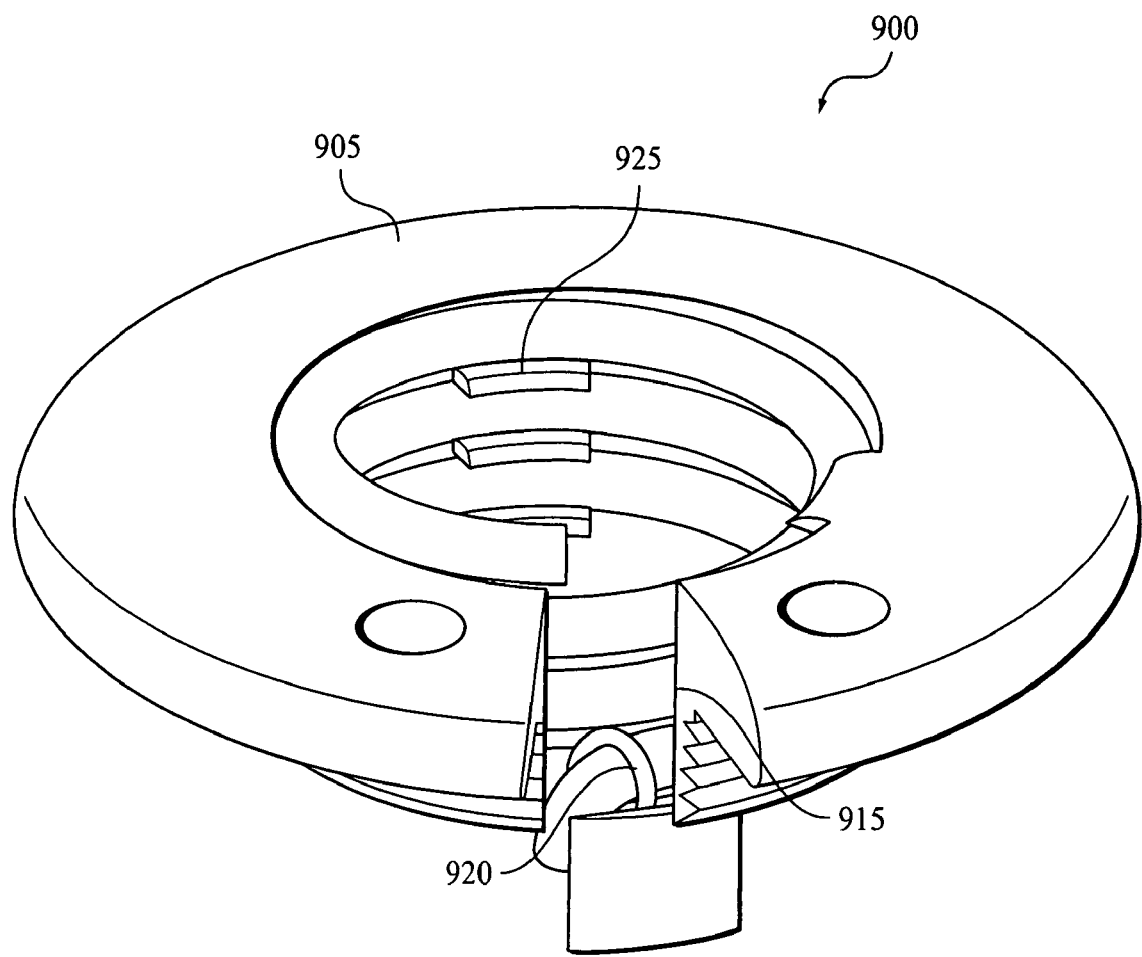
FIG. 9 illustrates a perspective view of another embodiment of a device 900 for retaining an excess portion of a lead implanted in the brain of a patient.

Illustrated in FIG. 9 is another embodiment of device 900 for retaining at least a section of the excess portion of a lead implanted in or on a surface of a brain of a patient. In this embodiment, the device 900 includes a burr hole ring 905 having an aperture 910 and a lead retainer provided on an inside surface or substrate 915 of the burr hole ring 905 for retaining at least a section of the excess portion of the lead L. It will be appreciated that the burr hole ring 905 can include a clip 920 or other anchoring device on the inside surface 915 thereof below the lead retainer to secure the lead L in place.

In one embodiment, the lead retainer can include a plurality of tabs 925 extending radially inward from the inside surface 915 of the burr hole ring 905. The tabs 925 can provide a system of grooves between adjacent tabs 920. For example, the tabs 925 can be arranged on the inside surface 915 of the burr hole ring 905 in such a manner so as to create a screw thread-type groove. Thus, the excess portion of the lead L can be inserted into the system of grooves 925 to form a spring-like vertical coil of loops.

In one embodiment, the width of each groove can be less than an outside diameter of the lead L, but configured to accept the lead L by increasing the width of the groove a distance at least as great as the outside diameter of the lead L when a force is being applied to insert the lead L into the groove. When the force is released, the width of the groove is reduced to retain the lead L.

In one embodiment, the excess portion of the lead L can be formed into a coiling configuration that can satisfy at least one MRI safety concern. For example, a coiling configuration can reduce a change in temperature at electrical contacts of the lead L when the patient is undergoing an MRI procedure or subjected to an otherwise substantial electromagnetic field. In one embodiment, the heating of the electrode contacts, while the patient is undergoing an MRI procedure or subjected to an otherwise substantial electromagnetic field, can be minimized by configuring the excess portion of the lead L into one or more loops. While not wishing to be bound by theory, the formation of the excess portion of the lead L into loops can minimize this "antenna" effect and, thus, minimize excessive heating of the electrode contacts. In one embodiment, the change in temperature at the electrodes decreases as the number of loops of the excess portion of the lead L increases.

It will be appreciated that a burr hole cap can be used with devices 600, 700, and 800 to anchor the lead L in place and prevent movement thereof. The burr hole cap can be dome-shaped and configured to be inserted into the aperture of the burr hole device to trap the lead therebetween. Alternatively, a clip or other anchoring means can be provided with devices 600, 700, 800, and 900 to anchor the lead L in place and prevent movement thereof.

It will be appreciated that a burr hole cap (that is used in conjunction with burr hole rings) can be modified to include a device for retaining at least a section of the excess portion of a lead. For example, the burr hole cap may include lead retainers extending therefrom as shown in FIGS. 4A and 6A and described above. Alternatively, the burr hole cap may include lead retainers that can be pivotally connected thereto as shown in FIG. 7 and described above. Another option is to provide a guiding groove in the burr hole cap as shown in FIG. 8A and described above.

Figure 10A:
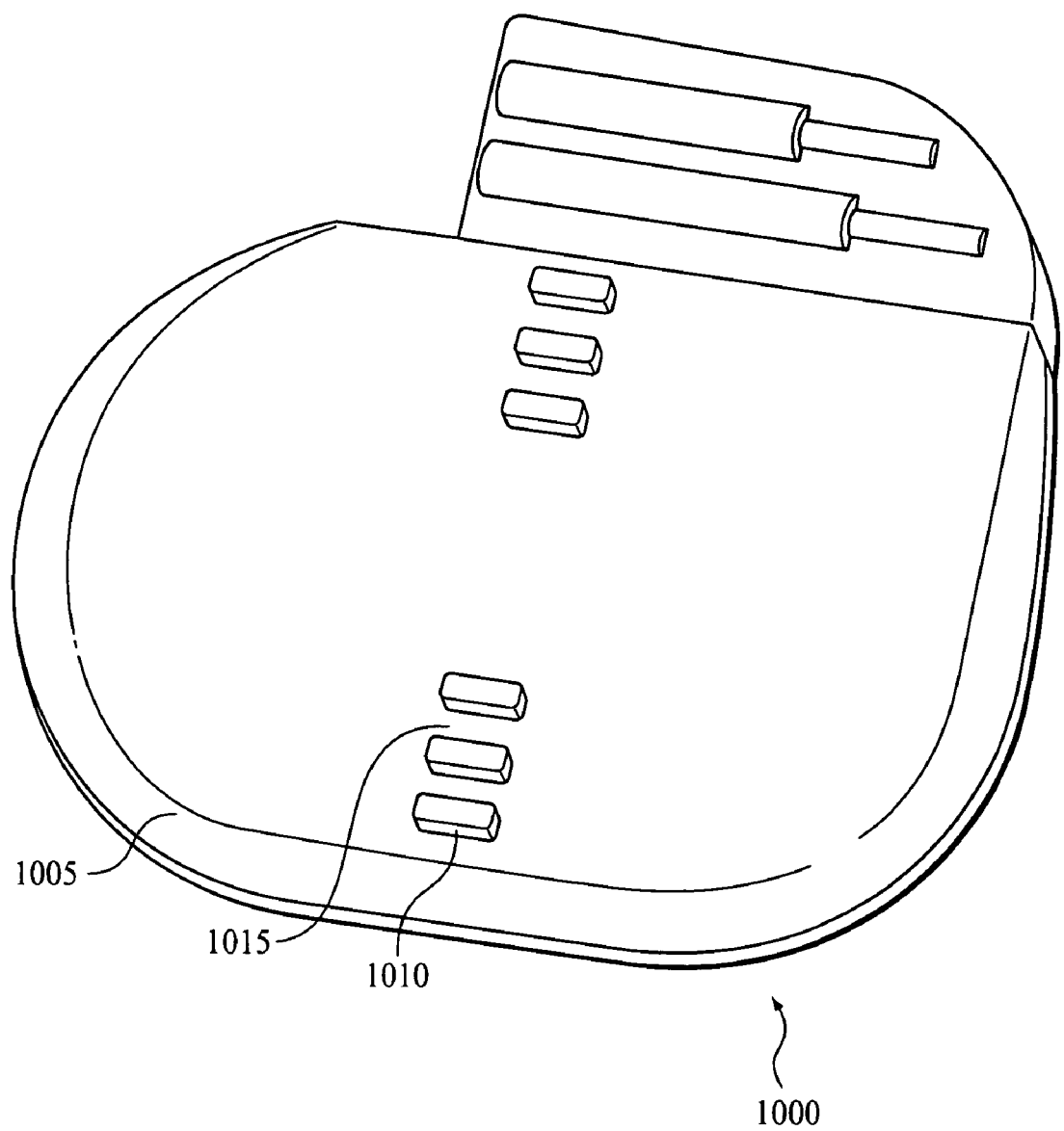
FIG. 10A illustrates a perspective view of another embodiment of a device 1000 for retaining an excess portion of a lead exiting from an IPG.
Figure 10B:
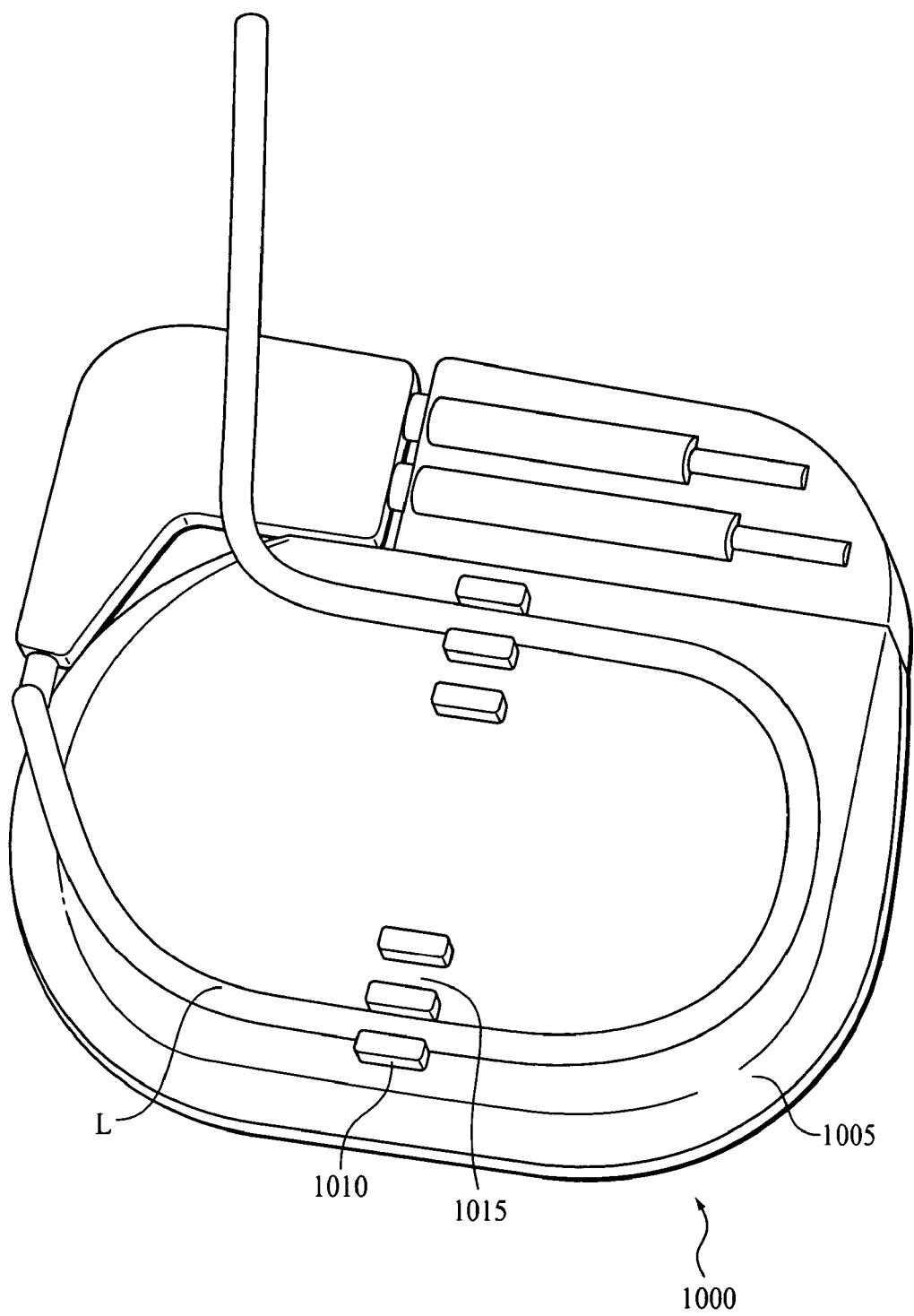
FIG. 10B illustrates a perspective view of the device 1000 with lead L in a coiled configuration.

FIGS. 10A-10B illustrate one embodiment of a device 1000 for retaining an excess portion of a lead or extension lead exiting from an IPG. The device 1000 can be configured to be used with an IPG to manage an excess portion of the lead exiting the IPG. It will be appreciated that the device 1000 may be used with other types of IPGs including, but not limited to, spinal cord stimulators, bladder stimulators, bowel stimulators, cardiac pacemakers, implantable cardioverter defibrillators, vagal nerve stimulators, having different sizes and shapes. The device 1000 may be used alone or in combination with the devices 400, 600, 700, 800, 900 discussed above to maximize MRI safety effectiveness.

In one embodiment, the device 1000 includes an IPG housing or substrate 1005 having lead retainer tabs 1010 extending therefrom to form grooves 1015 therebetween for receiving a section of the excess portion of the lead L and/or extension lead (collectively referred to as the "lead L"). It will be appreciated that the IPG housing 1005 may take the form of any commercially available IPG or any other shape.

In one embodiment, the tabs 1010 and resulting grooves 1015 may be configured in an "east-west" configuration as shown in FIG. 10B. In another embodiment, the tabs 1010 and resulting grooves 1015 may be configured in a "north-south" configuration or any combination of the two configurations. Of course, each guide may be positioned in any angular position with respect to another guide other than "north-south" or "east-west."

In one embodiment, the width of each groove 1015 can be less than an outside diameter of the lead L, but configured to accept the lead L by increasing the width of the groove 1015 a distance at least as great as the outside diameter of the lead L when a force is being applied to insert the lead L into the groove 1015. When the force is released, the width of the groove 1015 is reduced to retain the lead L.

In an example operation, the IPG is implanted and the surgeon can begin to insert the excess portion of the lead L into the grooves 1015 thereby forming a coil of the excess portion of the lead L that is retained within the grooves 1015. The excess portion of the lead L may be coiled in a clockwise fashion and inserted into the grooves 1015 until all of the excess portion of the lead L has been used up. Although the figures illustrate that the coiling may take place in a clockwise fashion, it will be appreciated that the coiling may take place in a counterclockwise fashion. Although FIG. 10B illustrates one embodiment of a coiling configuration, it will be appreciated that the excess portion of the lead L may be formed into any desired coiling configuration.

In one embodiment, the excess portion of the lead L can be formed into a coiling configuration that can satisfy at least one MRI safety concern. For example, a coiling configuration can reduce a change in temperature at electrical contacts of the lead L when the patient is undergoing an MRI procedure or subjected to an otherwise substantial electromagnetic field. In one embodiment, the heating of the electrode contacts, while the patient is undergoing an MRI procedure or subjected to an otherwise substantial electromagnetic field, can be minimized by configuring the excess portion of the lead L into one or more loops. While not wishing to be bound by theory, the formation of the excess portion of the lead L into loops can minimize this "antenna" effect and, thus, minimize excessive heating of the electrode contacts. In one embodiment, the change in temperature at the electrodes decreases as the number of loops of the excess portion of the lead L increases.

Figure 11A:
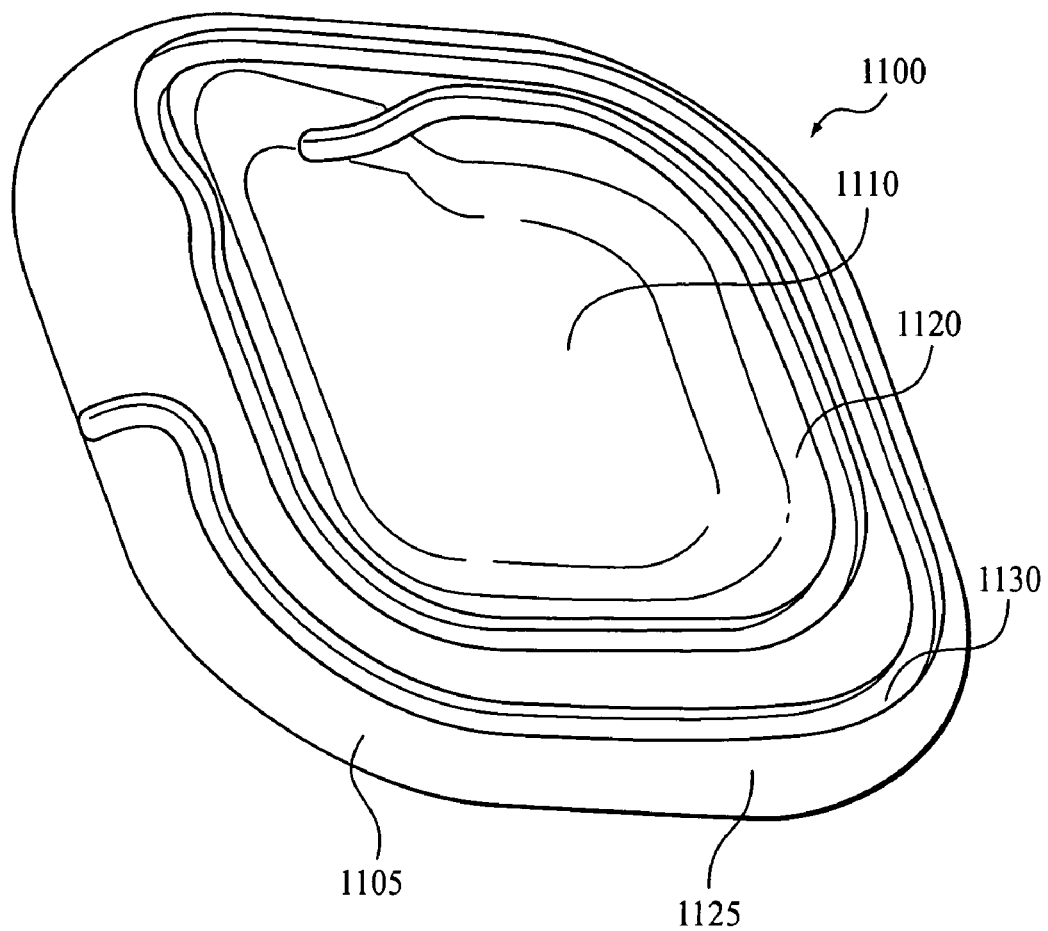
FIG. 11A illustrates a perspective view of another embodiment of a device 1100 for retaining an excess portion of a lead exiting from an IPG.
Figure 11B:
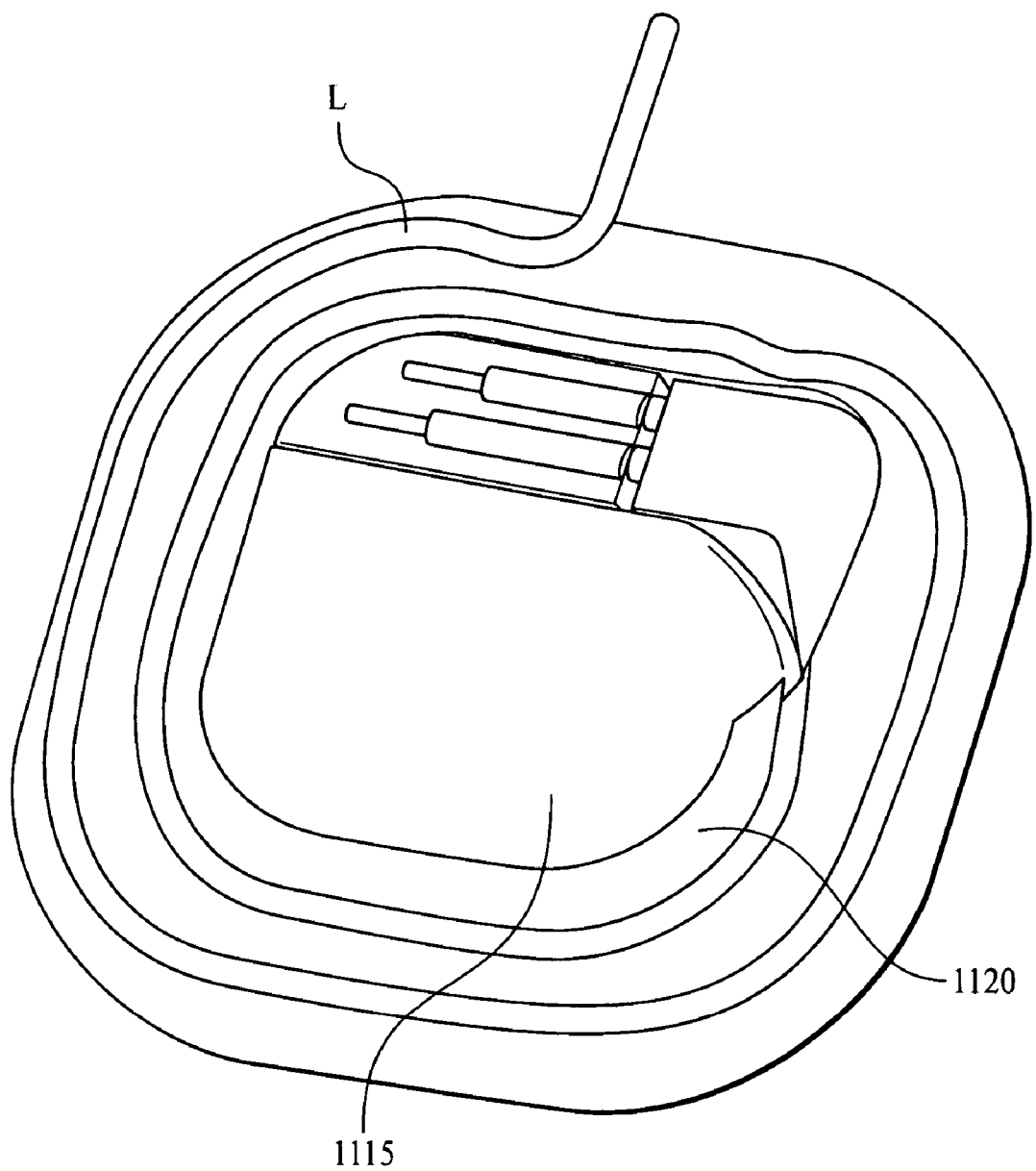

FIGS. 11A-11B illustrate another embodiment of a device 1100 for retaining an excess portion of a lead exiting from an IPG. The device 1100 is configured to be used with an IPG to manage an excess portion of the lead exiting the IPG. It will be appreciated that the device 1100 may be used with other IPGs including, but not limited to, spinal cord stimulators, bladder stimulators, bowel stimulators, cardiac pacemakers, implantable cardioverter defibrillators, vagal nerve stimulators, having different sizes and shapes. The device 1100 may be used alone or in combination with the devices 400, 600, 700, 800, 900 discussed above to maximize MRI safety effectiveness.

The device 1100 comprises a shoe, cover, or substrate 1105 having a cavity 1110 disposed therein for receiving the exterior body of an IPG housing 1015. In one embodiment, the cavity 1110 can be dimensioned such that it matches or is slightly larger than the exterior dimensions of any particular commercially available IPG resulting in a relatively snug fit when such commercially available IPG is inserted into the cavity 1110.

Extending around at least a portion of the cavity 1110 is a retention lip 1120 that is flexible enough to permit the IPG housing 1115 to be inserted into the cavity 1110, yet resilient enough to secure the IPG housing 1115 in the cavity 1110 once it has been inserted. On a perimeter portion 1125 of the shoe 1105, a guiding groove or lead retainer 1130 can be provided for receiving the excess portion of the lead L that exits the IPG housing 1115. Optionally, the shoe 1105 may include lead retainer tabs (not shown) extending therefrom to form grooves (not shown) therebetween for receiving the lead L.

In one embodiment, the width of each groove 1130 can be less than an outside diameter of the lead L, but configured to accept the lead L by increasing the width of the groove 1130 a distance at least as great as the outside diameter of the lead L when a force is being applied to insert the lead L into the groove 1130. When the force is released, the width of the groove 1130 is reduced to retain the lead L.

In one embodiment, the shoe 1105 is unitary in construction such that it is constructed of a biocompatible flexible material. Examples of suitable materials include polyurethane, silicone elastomers, and other elastomeric materials. In another embodiment, the shoe 1105 may be constructed in two or more separate parts where the retention lip 1120 may be a separate component from the shoe 1105. In this embodiment, the retention lip 1120 may be constructed of a biocompatible material such as polyurethane, silicone elastomers, or another elastomeric material, while the rest of the shoe 1105 may be constructed of a more rigid material such as polycarbonate, polypropylene, polyethylene, or nylon.

In an example operation, the IPG housing 1015 can be installed into the cavity 1110 of the device 1100 ensuring that the IPG housing 1015 is secured in place by the retention lip 1120. Once the IPG housing 1015 is secured in the device 1100, the excess portion of the lead L can be coiled as shown in FIG. 11B. In one embodiment, the excess portion of the lead L can be inserted into the groove 1130 beginning with a portion of the groove 1130 closest to the electrical connection point between the IPG housing 1115 and the lead L. The excess portion of the lead L can be coiled around the IPG housing 1115 by continuing to insert it into the groove 1130 in a clockwise fashion until all of the excess length has been used up. Although the figures illustrate that the coiling takes place in a clockwise fashion, it will be appreciated that the coiling may take place in a counterclockwise fashion. Although FIG. 11B illustrates one embodiment of a coiling configuration, it will be appreciated that the excess extension lead length may be formed into any desired coiling configuration.

In one embodiment, the excess portion of the lead L can be formed into a coiling configuration that can satisfy at least one MRI safety concern. For example, a coiling configuration can reduce a change in temperature at electrical contacts of the lead L when the patient is undergoing an MRI procedure or subjected to an otherwise substantial electromagnetic field. In one embodiment, the heating of the electrode contacts, while the patient is undergoing an MRI procedure or subjected to an otherwise substantial electromagnetic field, can be minimized by configuring the excess portion of the lead L into one or more loops. While not wishing to be bound by theory, the formation of the excess portion of the lead L into loops can minimize this "antenna" effect and, thus, minimize excessive heating of the electrode contacts. In one embodiment, the change in temperature at the electrodes decreases as the number of loops of the excess portion of the lead L increases.

In another embodiment and under certain circumstances, the excess portion of the lead may not need to be coiled around the burr hole and/or the IPG. For example, the coiling of the excess portion of the lead may take place anywhere between the burr hole site and the IPG site.

Figure 12:
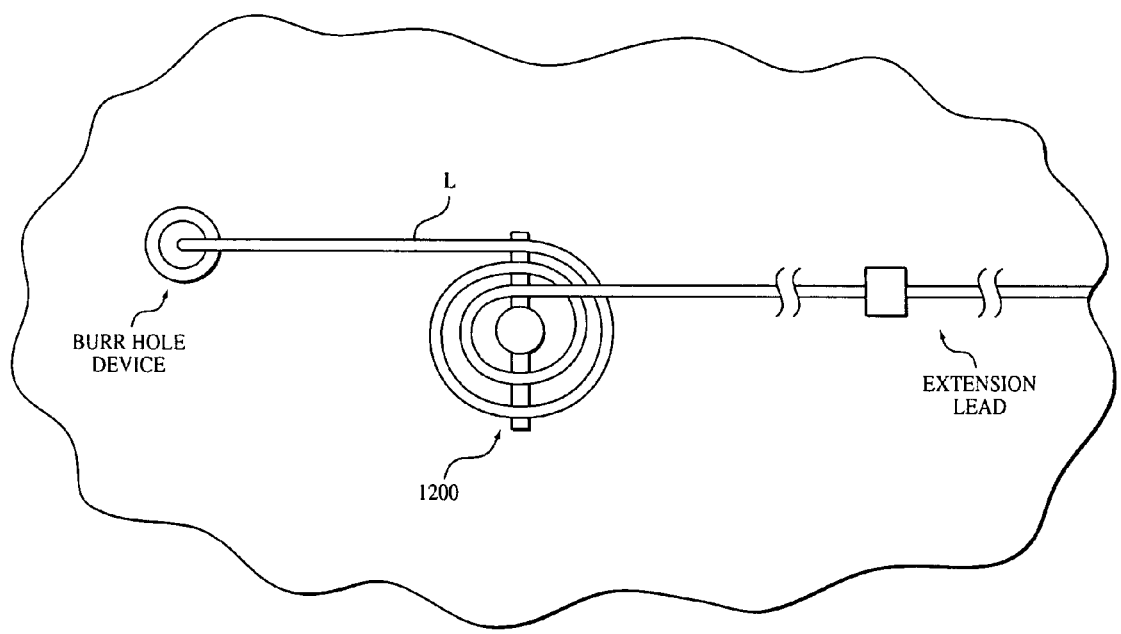
FIG. 12 illustrates a top plan view of another embodiment of a device 1200 for retaining an excess portion of a lead L implanted in the brain of a patient wherein the device 1200 is at a spaced-apart location from the burr hole.

FIG. 12 illustrates a device 1200 that can be used to retain the excess portion of the lead L between the burr hole site and the IPG site. The device 1200 can be similar in structure to the device 400 described above and illustrated in FIG. 4A; however, the device 1200 can be secured to the skull or another portion of a patient as desired in between the burr hole and the IPG. In this embodiment, the device 1200 is disposed within the patient away from the burr hole device. Accordingly, the coiling of the excess portion of the lead L occurs away from the burr hole device. Obviously, the device 1200 can take the form of or include many of the features and characteristics of the devices (e.g., 400, 600, 700, 800, 900, 1000, and 1100) discussed above. Moreover, the device 1200 can take the form of any structure that is capable of retaining an excess portion of the lead in a variety of coiling configurations (e.g., see FIGS. 5A-5F).

As used herein, the term "lead" refers to any elongated medical apparatus having proximal and distal ends, the distal end being extendable into or onto a surface of a target site of the brain through a burr hole. The lead is to be anchored relative to a known location within the burr hole, so that the location of the distal end of the apparatus at, near, or within the target site of the brain may be controlled. The term lead may refer to an electrode providing electrical stimulation or a parenchymal catheter for infusing pharmaceutical agents. Where a positioned apparatus is either an electrical stimulation lead or catheter extending through a burr hole, the distal end of the positioned apparatus typically will be situated within or on a surface of the brain, and the desired control of that end will be holding the distal end as stationary as possible.

Although the present application focuses on the use of excess lead management devices with neurostimulation system components (e.g., burr hole devices and IPGs), the present invention also has applicability for use with other permanent and temporary implantable intracranial devices such as monitoring and recording devices. Examples include, but are not limited to, intracranial pressure monitors, CSF diversion/temporary or permanent fixed rate or programmable shunting devices, implantable microinfusion pumps and any other device containing material which may induce currents, heat, or other undesirable side-effects. Additionally, there may be other applications for the present invention including use as a guide to aid in the positioning of other implantable devices such as intracranial pressure monitoring devices.

Furthermore, the present invention has applicability for use in other areas such as cardiac pacing, spinal cord stimulation, cranial nerve stimulators (such as vagus nerve stimulators, trigeminal nerve stimulators, and peripheral nerve stimulators used for a wide spectrum of disorders such as various pain syndromes, cardiovascular disorders, psychiatric disorders and movement disorders), or other implantable devices.

It will be appreciated that the excess lead retaining devices discussed above can be modified to be used with cardiac pacing devices, spinal cord stimulation devices, and other neurological and non-neurological implantable electrode stimulation, infusion, monitoring, or recording devices.

In another embodiment, components of the neuromodulation system and/or the other devices discussed above (e.g., cardiac pacing, spinal cord stimulation, intracranial pressure monitoring devices, etc.) can be designed to include decoupling, tuning, and/or filtering circuitry to reduce the likelihood of current induction and subsequent heating of the electrode contacts. For example, the devices could include filtering and/or tuning circuitry that is tuned to the resonant frequency of the RF energy radiated by the MRI system. This circuitry can also serve as a choke or a current/heat sink in the system. Such circuitry can be integrated into any of the aforementioned embodiments described above and can make a device compatible with various MRI systems, designs, sequences and manufactures. The circuitry can make a device compatible by selectively passing or blocking induced signals having determine characteristics in the lead based on imaging signal patterns generated by the MRI sequence in use.

In one embodiment, the aforementioned circuitry could be used to identify the device and render the MRI system output safe with respect to generation of significant current. For example, this circuitry can be incorporated into any one of the components of a neurmodulation system such that the circuitry could provide the MRI system information about itself so that a switch could be set in the MRI system to allow a pre-defined, neuromodulation-safe sequence to be run.

The following examples are given for the purpose of demonstrating the potential effects of looping or coiling the excess portion of the lead with respect to MRI safety and should not be construed as limitations on the scope or spirit of the present invention.

EXAMPLE 1

To test the effects of looping or coiling the excess portion of the lead around the burr hole, two Activa® Tremor Control System (Medtronic, Minneapolis, Minn.) were used. Each Activa® Tremor Control System included a Soletra® quadripolar neurostimulator (Model 7426), a quadripolar lead (Model 3387-40) having a length of 40 cm and containing four individually insulated conductors that connect to four electrode contacts, and an extension lead (Model 7495-51) having a length of 51 cm that connects the neurostimulator to the lead.

The Activa® Tremor Control Systems were then installed into a plexiglass phantom designed to approximate the size and shape of the head and torso of a human subject. The dimensions of this phantom were, as follows: "head" portion—width, 16.5-cm; length, 29.2-cm; height, 16.5-cm; "torso" portion—width, 43.2-cm; length, 61.0-cm; height, 16.5-cm. Since most heating during MRI is due to eddy currents in the head and body, it was unnecessary to include extremities in this phantom for the assessment of MRI-related heating of a metallic object.

The phantom was filled to a depth of 91-mm with a semi-solid gel that was prepared to simulate the thermal convection properties of human tissue. This was accomplished using a gelling agent (polyacrylic acid, PAA, Aldrich Chemical) in an aqueous solution. Thus, 5.85 grams of PAA and 0.8 grams of NaCl per liter of distilled water were used to make the semi-solid gel. This produced an acceptable dielectric constant and an acceptable conductivity for evaluation of MRI-related heating of a metallic implant or device. This basic experimental set-up has been used in several prior investigations published in the peer-reviewed literature. Because there was no blood flow associated with this experimental set-up, it represents an extreme condition simulated for MRI-related heating of the neurostimulation system.

A plastic frame with adjustable posts was placed at the bottom of the phantom and allowed for variable positioning and support of the neurostimulators, extensions, and leads within the phantom. The individual system components were secured to the posts by various means using non-metallic fasteners (e.g., sutures, plastic clips, putty). The use of the plastic frame and posts permitted consistent placement of the neurostimulators within the phantom and allowed the extensions and leads to be routed to approximate common clinical practice, as described below. These experimental procedures facilitated proper and repeatable approximation of the standard in vivo positioning and orientation of the devices.

In consideration of the fact that positional differences can impact MRI-related heating of neurostimulators and in order to simulate the intended in vivo use of the neurostimulation systems, careful attention was given to the positioning of the two neurostimulators, extensions, and leads within the phantom. The manufacturer's (Medtronic, Minneapolis, Minn.) product insert information was followed along with the recommendations of a neurosurgeon with extensive DBS implant experience.

The two neurostimulators were placed in the upper left and right quadrants of the "thorax" portion of the phantom. They were positioned within 2-cm from the surface of the gel, separated by a distance of approximately 30-cm. The extensions were connected to the neurostimulators and the excess lengths were wrapped two times around the perimeter of the neurostimulators. Care was taken not to bend, kink, or stretch the extension wires.

In this experiment, two devices for retaining the excess portion of the lead (devices 400 and 700 from above) were used interchangeably and positioned within the phantom. The leads were positioned within the phantom in an area believed to represent the location of a conventional "burr hole" and multiple sections of the excess portion of each lead were inserted into the lead retainers and different numbers of loops were formed. For each test, the number of loops was adjusted such that there were tests run with full loops (e.g., one and two loops) and partial loops (e.g., half and one and a half loops). The electrodes were positioned relative to approximate a bilateral in vivo use of these devices, at a depth of 41-mm in the gel-filled phantom to approximate the typical placement for a DBS target (i.e., the thalamus).

Temperature recordings were obtained using an MR-compatible, Model 790 Fluoroptic Thermometry System (Luxtron, Santa Clara, Calif.) that has been used in many previously published studies conducted to assess MRI-related heating for implants and devices. This thermometry system has small fiber-optic probes (0.5 mm diameter, Model SSF) that respond rapidly (response time, 0.25 seconds), with an accuracy and resolution of ±0.5° C. accuracy within 50° C. of the calibration point.

Four fluoroptic thermometry probes were positioned to record representative sites for the neurostimulation systems that would generate the greatest heating during MRI based on previously published literature previously conducted and pilot experiments. For the neurostimulators, extensions, and electrodes evaluated in this study, the effects of induced currents generated during MRI will be concentrated at the electrodes of the leads. Thus, thermometry probes were positioned on or near the leads, as follows:

1, R-Probe, placed within 0.1-mm on the center of the distal electrode of the right lead;

2, L-Probe, placed within 0.1-mm on the center of the distal electrode of the left lead;

3, M-Probe, placed between the two distal electrodes of the leads; and

4, Reference Probe, placed at a remote position, from the electrodes, within 1-cm from the edge of the "head" portion of the phantom (i.e., to record a reference temperature).

MR imaging was performed on the gel-filled phantom and neurostimulation systems using a 1.5 Tesla/64 MHz MR system (Siemens Medical Systems, Iselin, N.J.) and the transmit/receive body RF coil. During this experiment, the neurostimulators were programmed to the "off" mode (i.e., no stimulation was delivered) and set to 0 voltage, as is the common clinical practice during MR imaging. For each experiment, MR imaging was conducted for a total of 15-min. (i.e., worst case imaging time).

Figure 13:
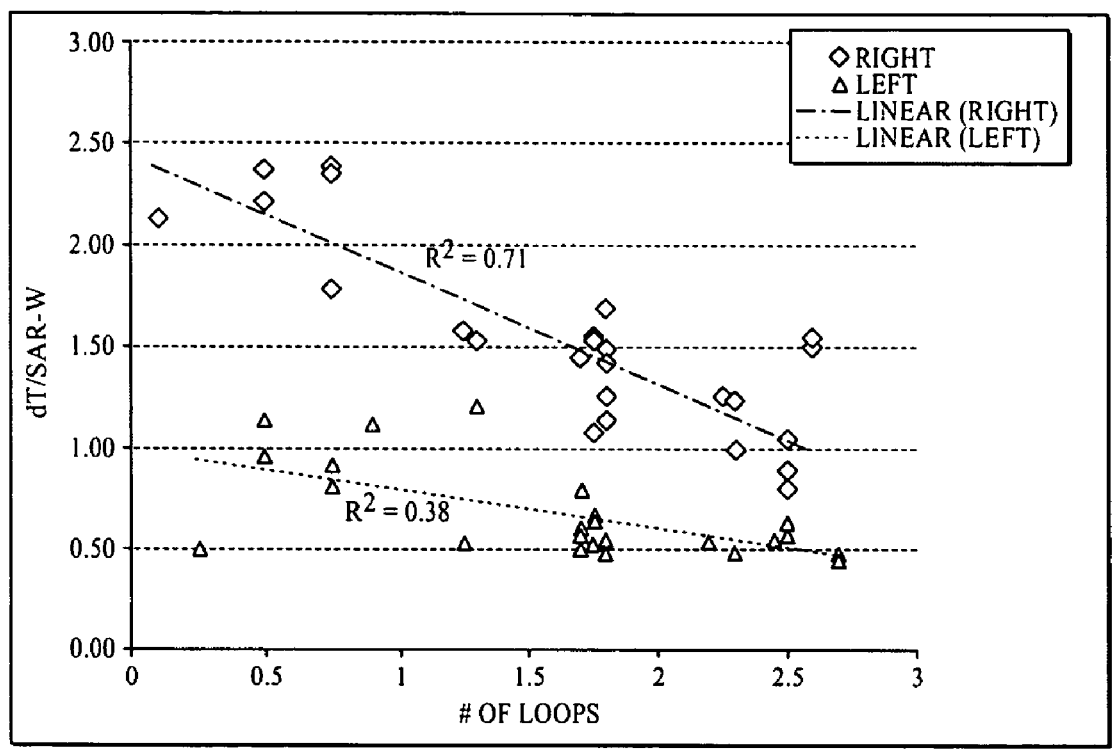
FIG. 13 illustrates a graph representing the effects of loops around the burr hole on MRI-related heating at the implanted electrode contacts of the lead in a 1.5-Tesla MR system, where the x-axis shows the number of loops created and the y-axis is represented in temperature units normalized to whole body SAR.

Illustrated in FIG. 13 is a graph representing the effects of loops around the burr hole on heating at the implanted electrode contacts of the lead. The x-axis shows the number of loops created and the y-axis is represented in temperature units normalized to whole body SAR. Each point is a separate MR scan. As there was no apparent effect of clockwise versus counterclockwise rotations, no distinction is made in this respect on the graph. As shown in the graph in FIG. 13, the temperature at the electrode contacts decreases as the number of loops increases.

EXAMPLE 2

In a slightly different experiment, MR imaging was performed on the gel-filled phantom and neurostimulation systems using a 3.0 Tesla/64 MHz MR system (Siemens Medical Systems, Iselin, N.J.) and the transmit/receive head RF coil. In this experiment, the same Activa® Tremor Control Systems, phantom, and thermometry system were used as in Example 1. Also, the components were positioned in substantially the same locations within the phantom and the testing process was the same as in Example 1. However, the device for retaining the excess portion of the lead used in this experiment was the device 700 from above.

Figure 14:
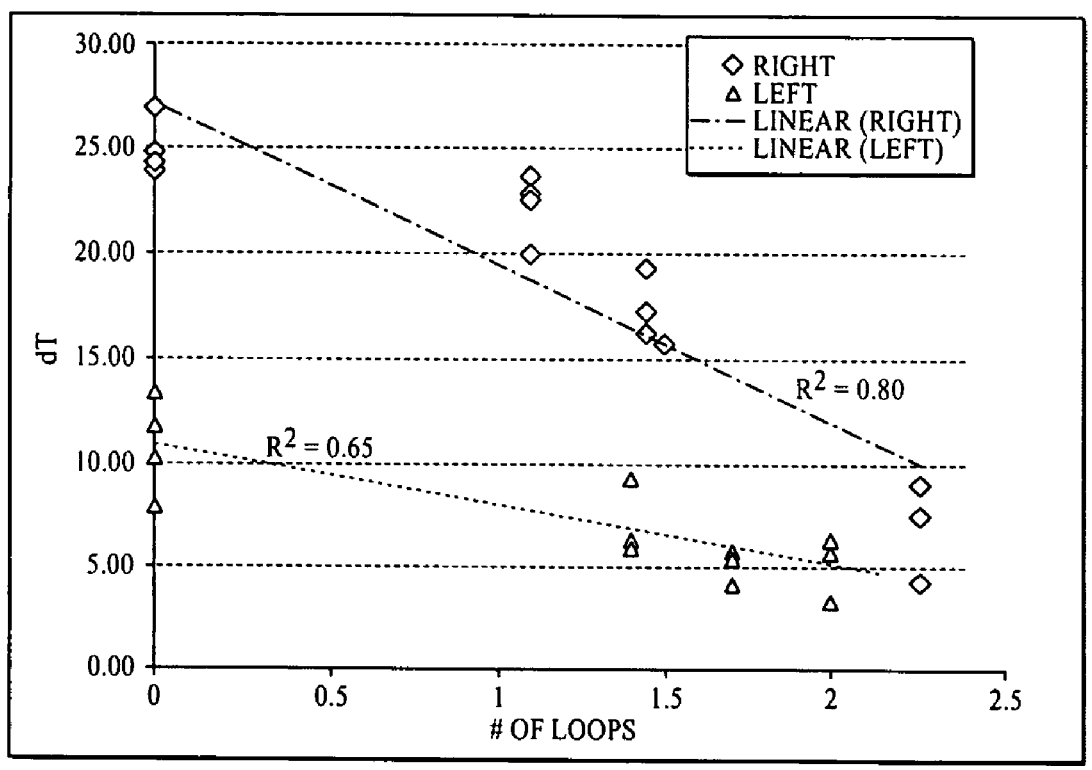
FIG. 14 illustrates a graph representing the effects of loops around the burr hole on MRI-related heating at the implanted electrode contacts of the lead where the x-axis shows the number of loops created and the y-axis shows the change in temperature of the electrode contacts when exposed to a 3.0-Tesla MR system.

Illustrated in FIG. 14 is a graph representing the effects of loops around the burr hole on heating at the implanted electrode contacts of the lead. The x-axis shows the number of loops created and the y-axis shows the change in temperature of the electrode contacts when exposed to MRI. Once again, each point is a separate MR scan. As there was no apparent effect of clockwise versus counterclockwise rotations, no distinction is made in this respect on the graph. As shown in the graph in FIG. 14, the change in temperature at the electrode contacts decreases as the number of loops increases.

Although the invention has been described with reference to the preferred embodiments, it will be apparent to one skilled in the art that variations and modifications are contemplated within the spirit and scope of the invention. The drawings and description of the preferred embodiments are made by way of example rather than to limit the scope of the invention, and it is intended to cover within the spirit and scope of the invention all such changes and modifications.

What is claimed is:

1. A device for retaining an excess portion of a lead that is implanted within or on a surface of a brain of a patient wherein access to the brain is provided through a burr hole in a skull of a patient, the device comprising:

a burr hole ring having an aperture configured to receive the lead therethrough and an outside surface, the burr hole ring being configured to be secured to the skull wherein the aperture in the burr hole ring is in general alignment with the burr hole, the outside surface of the burr hole ring including a spiral groove that extends from the aperture to at least one outlet periphery of the outside surface of the burr ring, the spiral groove dimensioned such that the excess portion of the lead can be stored in at least one loop in the spiral groove;

wherein the groove includes a plurality of concentric grooves extending circumferentially around the outside surface of the burr hole ring, and at least one generally radial groove in the outside surface communicating with the plurality of concentric grooves, the radial groove extending to an outlet at a periphery of the outside surface of the burr hole ring.

2. The device of claim 1 wherein the burr hole ring is formed from a resilient material.

3. The device of claim 1 wherein at least a section of the excess portion of the lead is retained in the retaining means in one of a plurality of different coiling configurations.

* * * * *